(12) United States Patent
Echigo et al.

(10) Patent No.: US 9,828,355 B2
(45) Date of Patent: Nov. 28, 2017

(54) COMPOUND, MATERIAL FOR FORMING UNDERLAYER FILM FOR LITHOGRAPHY, UNDERLAYER FILM FOR LITHOGRAPHY AND PATTERN FORMING METHOD

(71) Applicant: Mitsubishi Gas Chemical Company, Inc., Tokyo (JP)

(72) Inventors: Masatoshi Echigo, Kanagawa (JP); Takashi Makinoshima, Kanagawa (JP); Naoya Uchiyama, Okayama (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 14/766,697

(22) PCT Filed: Feb. 4, 2014

(86) PCT No.: PCT/JP2014/052524
§ 371 (c)(1),
(2) Date: Aug. 7, 2015

(87) PCT Pub. No.: WO2014/123102
PCT Pub. Date: Aug. 14, 2014

(65) Prior Publication Data
US 2015/0376158 A1 Dec. 31, 2015

(30) Foreign Application Priority Data
Feb. 8, 2013 (JP) .................. 2013-023529

(51) Int. Cl.
*G03F 7/11* (2006.01)
*G03F 7/26* (2006.01)
*H01L 21/311* (2006.01)
*C07D 311/82* (2006.01)
*C07D 311/86* (2006.01)
*G03F 7/075* (2006.01)
*G03F 7/09* (2006.01)

(52) U.S. Cl.
CPC .......... *C07D 311/82* (2013.01); *C07D 311/86* (2013.01); *G03F 7/0752* (2013.01); *G03F 7/094* (2013.01); *G03F 7/11* (2013.01); *G03F 7/26* (2013.01); *H01L 21/31116* (2013.01); *H01L 21/31144* (2013.01)

(58) Field of Classification Search
None
See application file for complete search history.

(56) References Cited

U.S. PATENT DOCUMENTS

| 2,100,798 | A |   | 11/1937 | Dilthey et al. |   |
|---|---|---|---|---|---|
| 2,546,872 | A | * | 3/1951 | Schmid | C07D 311/78 549/382 |
| 3,947,468 | A |   | 3/1976 | Hall et al. |   |
| 4,579,758 | A |   | 4/1986 | Dorsch et al. |   |
| 5,332,648 | A |   | 7/1994 | Kihara et al. |   |
| 6,784,228 | B2 | * | 8/2004 | Ogura | C07D 311/78 523/466 |
| 9,316,913 | B2 |   | 4/2016 | Echigo et al. |   |

| 2002/0106909 | A1 | 8/2002 | Kato et al. |
|---|---|---|---|
| 2003/0092852 | A1 | 5/2003 | Ogura et al. |
| 2004/0186776 | A1 | 9/2004 | Llach |

(Continued)

FOREIGN PATENT DOCUMENTS

| EP | 1 300 403 A1 | 4/2003 |
|---|---|---|
| EP | 2 743 769 A1 | 6/2014 |
| JP | H01-283280 A | 11/1989 |
| JP | H05-134415 A | 5/1993 |
| JP | H06-049402 A | 2/1994 |
| JP | H06-242607 A | 9/1994 |
| JP | H7-215833 A | 8/1995 |
| JP | H10-25220 A | 1/1998 |
| JP | H11-072925 A | 3/1999 |
| JP | 2002-214769 A | 7/2002 |

(Continued)

OTHER PUBLICATIONS

Machine translation of JP 2006-036648 (2006).*
Machine transaltion of WO 2007/097457 (2007).*
International Search Report dated Mar. 25, 2014 for PCT/JP2014/052524 and English translation of the same (8 pages).

(Continued)

*Primary Examiner* — Martin Angebranndt
(74) *Attorney, Agent, or Firm* — Fitch, Even, Tabin & Flannery LLP

(57) ABSTRACT

The material for forming an underlayer film for lithography of the present invention contains a compound represented by the following general formula (1).

[Formula 1]

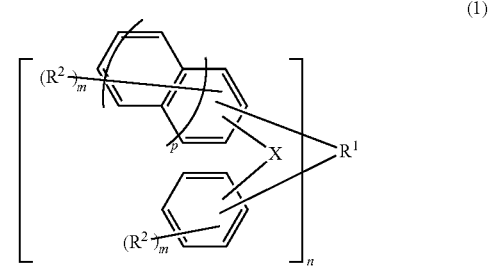

(1)

(in formula (1), each X independently represents an oxygen atom or a sulfur atom, $R^1$ represents a single bond or a 2n-valent hydrocarbon group having 1 to 30 carbon atoms, the hydrocarbon group may have a cyclic hydrocarbon group, a double bond, a hetero atom or an aromatic group having 6 to 30 carbon atoms, and each $R^2$ independently represents a linear, branched or cyclic alkyl group having 1 to 10 carbon atoms, an aryl group having 6 to 10 carbon atoms, an alkenyl group having 2 to 10 carbon atoms, or a hydroxyl group, provided that at least one $R^2$ represents a hydroxyl group, each m is independently an integer of 1 to 4, n is an integer of 1 to 4, and p is 0 or 1.)

10 Claims, No Drawings

(56) References Cited

U.S. PATENT DOCUMENTS

| | | |
|---|---|---|
| 2004/0197709 A1 | 10/2004 | Arase et al. |
| 2005/0074695 A1 | 4/2005 | Nakamura |
| 2005/0255712 A1 | 11/2005 | Kato et al. |
| 2007/0059632 A1* | 3/2007 | Oguro ............... C07D 311/82 430/270.1 |
| 2007/1072759 | 7/2007 | Tsutomu Ogihara et al. |
| 2008/0138744 A1 | 6/2008 | Hatanaka et al. |
| 2008/0153031 A1* | 6/2008 | Echigo ............... G03F 7/0382 430/281.1 |
| 2009/0171061 A1 | 7/2009 | Sue et al. |
| 2009/0261300 A1 | 10/2009 | Watanabe |
| 2010/0207516 A1 | 8/2010 | Moriwaki et al. |
| 2010/0316950 A1 | 12/2010 | Oguro et al. |
| 2011/0177459 A1 | 7/2011 | Ogihara et al. |
| 2011/0311920 A1* | 12/2011 | Kinsho ............... C07C 43/275 430/323 |
| 2012/0064725 A1 | 3/2012 | Kinsho et al. |
| 2012/0171611 A1 | 7/2012 | Ideno et al. |
| 2012/0184103 A1 | 7/2012 | Ogihara et al. |
| 2012/0228584 A1 | 9/2012 | Wigglesworth et al. |
| 2013/0056653 A1 | 3/2013 | Hatakeyama et al. |
| 2013/0150627 A1 | 6/2013 | Okada et al. |
| 2014/0186776 A1 | 7/2014 | Uchiyama et al. |
| 2014/0248561 A1* | 9/2014 | Echigo ............... C07D 311/96 430/281.1 |
| 2014/0319097 A1* | 10/2014 | Kim ............... C07D 491/107 216/47 |
| 2015/0090691 A1* | 4/2015 | Echigo ............... C07D 311/96 216/49 |
| 2015/0368224 A1 | 12/2015 | Echigo |
| 2015/0376157 A1* | 12/2015 | Echigo ............... C07C 69/734 430/270.1 |
| 2015/0376158 A1 | 12/2015 | Echigo et al. |
| 2015/0376202 A1* | 12/2015 | Echigo ............... C07D 493/04 430/323 |
| 2016/0145231 A1 | 5/2016 | Echigo et al. |

FOREIGN PATENT DOCUMENTS

| | | |
|---|---|---|
| JP | 2002-334869 A | 11/2002 |
| JP | 2002-334896 A | 11/2002 |
| JP | 2002-341542 A | 11/2002 |
| JP | 2004-177668 A | 6/2004 |
| JP | 2004-271838 A | 9/2004 |
| JP | 2005-250434 A | 9/2005 |
| JP | 2005-326838 A | 11/2005 |
| JP | 2005-346024 A | 12/2005 |
| JP | 2006-036648 A | 2/2006 |
| JP | 2006-213634 A | 8/2006 |
| JP | 2007-019294 A | 1/2007 |
| JP | 2007-199653 A | 8/2007 |
| JP | 2007-226170 A | 9/2007 |
| JP | 2007-226204 A | 9/2007 |
| JP | 2007-262398 A | 10/2007 |
| JP | 2007-326847 A | 12/2007 |
| JP | 2008-065081 A | 3/2008 |
| JP | 2008-145539 A | 6/2008 |
| JP | 2008-239868 A | 10/2008 |
| JP | 2009-073738 A | 4/2009 |
| JP | 2009-098155 A | 5/2009 |
| JP | 2009-108313 A | 5/2009 |
| JP | 2009-155256 A | 7/2009 |
| JP | 2009-173623 A | 8/2009 |
| JP | 2010-170013 A | 8/2010 |
| JP | 2010-219295 A | 9/2010 |
| JP | 2011-068624 A | 4/2011 |
| JP | 2011-105887 A | 6/2011 |
| JP | 2011-150023 A | 8/2011 |
| JP | 2012-1687 A | 1/2012 |
| JP | 2012-145897 A | 8/2012 |
| JP | 2013-064978 A | 4/2013 |
| JP | 2013-087173 A | 5/2013 |
| WO | 02/14434 A1 | 2/2002 |
| WO | 03/017002 A1 | 2/2003 |
| WO | 2004/066377 A1 | 8/2004 |
| WO | 2005/111724 A1 | 11/2005 |
| WO | 2007/097457 * | 8/2007 |
| WO | 2007/097457 A1 | 8/2007 |
| WO | 2009-072465 A1 | 6/2009 |
| WO | 2009/119201 A1 | 10/2009 |
| WO | 2009/145224 A1 | 12/2009 |
| WO | 2011-034062 A1 | 3/2011 |
| WO | 2012/165507 A | 12/2012 |
| WO | 2013/024779 A1 | 2/2013 |
| WO | 2013/066067 * | 5/2013 |
| WO | 2013/066067 A1 | 5/2013 |

OTHER PUBLICATIONS

Nishiyama et al, Antioxidant activities of fused heterocyclic compounds, xanthene-2,7-diols with BHT or catechol skeleton, Polymer Degradation and Stability, 1998, vol. 62, No. 3, p. 529-534, Compound 5a.

Protiva et al., Neurotropic and psychotropic agents. CXXXIII. Collection of Czechoslovak Chemical Communications, 1979, vol. 44, No. 10, p. 2987-2996, compound II.

English Translation of JP H01-283280 A, Nov. 14, 1989.

Machine English Translation of JP 2008-239868 A, Oct. 9, 2008.

International Search Report dated Sep. 11, 2012 for International Application No. PCT/JP2012/070305 with English Translation (5 pages).

International Search Report dated Feb. 25, 2014 for International Application No. PCT/JP2014/051775 with English Translation (4 pages).

International Search Report dated May 13, 2014 for International Application No. PCT/JP2014/052530 with English Translation (8 pages).

Nakayama Tomonari et al., A New Three-Component Photoresist Based on Calix[4]resorcinarene Derivative, a Cross-Linker, and a Photo-Acid Generator, The Chemical Society of Japan, 1998, No. 71, pp. 2979-2984.

Dkazaki Shinji et al., Innovation of Photoresist Material Development, CMC Publishing Co., Ltd., Sep. 2009, pp. 211-259 (no English Translation available).

Sirkecioglu Okan et al., A Novel Synthesis of 14-(Hydroxymethylalkyl) Derivatives of Dibenzoxanthenes and 3,3-Dimethyl-4-(2-hydroxy-1-napthyl)benzo[f]chroman, Journal of Heterocyclic Chemistry, Mar. 1, 1998, vol. 35, No. 2, pp. 457-460.

Jha Amitabh and Beal Jennifer, "Convenient synthesis of 12H-benzo[a]xanthenes from 2-tetralone," Tetrahedron Letters, 2004, vol. 45, No. 49, pp. 8999-9001.

Singh Ritesh and Panda Gautam, "Scandium triflate-catalyzed one-pot domino approach towards general and efficient syntheses of unsymmetrical 9-substituted xanthene derivatives," Organic & Biomolecular Chemistry, 2010, vol. 8, No. 5, pp. 1097-1105.

Ghodratbeigi Mohsen et al., "Design, modeling and synthesis of molecular tweezers with self-assembly properties," Journal of Molecular Structure, 2011, vol. 990, No. 1, pp. 140-151.

Hagihara K. et al., "The effect of Ti-addition on plastic deformation and fracture behavior of directionally solidified NiAl/Cr(Mo) eutetic alloys," Intermetallics, 2006, vol. 14, No. 10, pp. 1326-1331.

Osman A-M, Reactions Between Chloro-p-benzoquinones and Beta-Naphtol, Journal of Organic Chemistry, 1957, vol. 22, pp. 342-344.

Ahmed Munir et al., The Direct Bradsher Reaction. Part I. Synthesis of Thiophen Analogues of Linear Polycyclic Hydrocarbons, Journal of the Chemical Society, Perkin Transactions I, 1973, pp. 1099-1103.

Sirringhaus Henning et al., Dibenzothienobisbenzothiophene—a novel fused-ring oligomer with high field-effect mobility, Journal of Materials Chemistry, 1999, vol. 9, pp. 2095-2101.

* cited by examiner

COMPOUND, MATERIAL FOR FORMING UNDERLAYER FILM FOR LITHOGRAPHY, UNDERLAYER FILM FOR LITHOGRAPHY AND PATTERN FORMING METHOD

CROSS-REFERENCE TO RELATED APPLICATIONS

This application is a, U.S. national phase application filed under 35 U.S.C. §371 of International Application PCT/JP2014/052524, filed on Feb. 4, 2014, designating the United States, which claims priority from Japanese Application Number 2013-023529, filed Feb. 8, 2013, which are hereby incorporated herein by reference in their entirety.

TECHNICAL FIELD

The present invention relates to a compound having a specific structure, a material for forming an underlayer film for lithography, the material containing the compound, an underlayer film for lithography, and a pattern forming method.

BACKGROUND ART

Semiconductor devices are manufactured through microfabrication by lithography using a photoresist material, but are required to be mabe finer by a pattern rule in accordance with the increase in integration degree and the increase in speed of LSI in recent years. In lithography using exposure to light, which is used as a general-purpose technique at present, the resolution is now approaching the intrinsic limitation associated with the wavelength of the light source.

A light source for lithography, for use in forming a resist pattern, has a shorter wavelength from a KrF excimer laser (248 nm) to an ArF excimer laser (193 nm). However, as the resist pattern is made finer and finer, there arises a problem of resolution or a problem of collapse of the resist pattern after development, and therefore there is demanded for making a resist film thinner. If the resist film is merely made thinner in response to such a demand, it is difficult to achieve a resist pattern having a film thickness sufficient for processing a substrate. Accordingly, there is increasingly required a process in which not only the resist pattern but also a resist underlayer film is prepared between a resist and a semiconductor substrate to be processed and the resist underlayer film is allowed to have a function as a mask at the time of processing the substrate.

Currently, as the resist underlayer film for such a process, various ones are known. Examples can include a resist underlayer film for lithography, having a selection ratio of dry etching rate close to the resist, unlike a conventional resist underlayer film having a high etching rate. As a material for forming such a resist underlayer film for lithography, there has been proposed a material for forming an underlayer film for multilayer resist process, containing a resin component having at least a substituent which releases a terminal group to form a sulfonic acid residue when a predetermined energy is applied, and a solvent (see, for example, Japanese Patent Laid-Open No. 2004-177668). In addition, examples can also include a resist underlayer film for lithography, having a smaller selection ratio of dry etching rate than the resist. As a material for forming such a resist underlayer film for lithography, there has been proposed a resist underlayer film material including a polymer having a specified repeating unit (see, for example, Japanese Patent Laid-Open No. 2004-271838). Furthermore, examples can also include a resist underlayer film for lithography, having a smaller selection ratio of dry etching rate than the semiconductor substrate. As a material for forming such a resist underlayer film for lithography, there has been proposed a resist underlayer film material including a polymer formed by co-polymerizing a repeating unit of acenaphthylene, and a substituted or non-substituted repeating unit having a hydroxy group (see, for example, Japanese Patent Laid-Open No. 2005-250434).

On the other hand, as a material for allowing such a resist underlayer film to have a high etching resistance, an amorphous carbon underlayer film is well known, which is formed by CVD using methane gas, ethane gas, acetylene gas, or the like as a raw material. However, there is demanded, in terms of process, a resist underlayer film material that can form a resist underlayer film in a wet process such as a spin coating method or screen printing.

In addition, as a material that is excellent in optical characteristics and etching resistance and that is capable of being dissolved in a solvent and being applied to a wet process, the present inventors have proposed a composition for forming an underlayer film for lithography, which contains a naphthalene formaldehyde polymer including a specified constituent unit, and an organic solvent (see, for example, International Publication Nos. WO 2009/072465 and WO 2011/034062).

Meanwhile, with respect to a forming method of an intermediate layer for use in forming a resist underlayer film in a three-layer process, for example, known are a forming method of a silicon nitride film (see, for example,Japanese Patent Laid-Open No. 2002-334869), and a CVD forming method of a silicon nitride film (see, for example, International Publication No. WO 2004/066377). In addition, as an intermediate layer material for a three-layer process, known is a material containing a silsesquioxane-based silicon compound (see, for example, Japanese Patent Laid-Open Nos. 2007-226170 and 2007-226204).

Patent Literature 1: Japanese Patent Laid-Open No. 2004-177668
Patent Literature 2: Japanese Patent Laid-Open No. 2004-271838
Patent Literature 3: Japanese Patent Laid-Open No. 2005-250434
Patent Literature 4: International Publication No. WO 2009/072465
Patent Literature 5: International Publication No. WO 2011/034062
Patent Literature 6: Japanese Patent Laid-Open No. 2002-334869
Patent Literature 7: International Publication No. WO 2004/066377
Patent Literature 8: Japanese Patent Laid-Open No. 2007-226170
Patent Literature 9: Japanese Patent Laid-Open No. 2007-226204

SUMMARY OF INVENTION

As described above, many materials for forming an underlayer film for lithography have been conventionally proposed, but there are no ones that not only have such a high solvent solubility as to be able to be applied to a wet process such as a spin coating method or screen printing, but also simultaneously satisfy heat resistance and etching resistance at a high level, and thus a new material is required to be developed.

The present invention has been made in view of the above problem. That is, an object thereof is to provide a compound, a material for forming an underlayer film for lithography, which can be applied to a wet process and which is useful for forming a photoresist underlayer film excellent in heat resistance and etching resistance, and a pattern forming method using the material.

The present inventors have intensively studied to solve the above problem, and as a result, have found that the above problem can be solved by using a compound or resin of a specified structure, thereby leading to the completion of the present invention.

That is, the present invention provides the following [1] to [10].

[1] A compound represented by the following general formula (1).

[Formula 1]

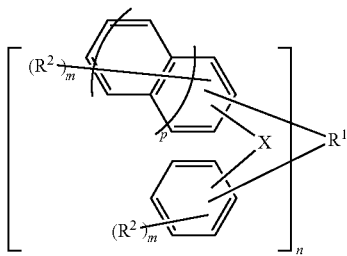

(1)

(in formula (1), each X independently represents an oxygen atom or a sulfur atom, $R^1$ represents a single bond or a 2n-valent hydrocarbon group having 1 to 30 carbon atoms, the hydrocarbon group may have a cyclic hydrocarbon group, a double bond, a hetero atom or an aromatic group having 6 to 30 carbon atoms, and each $R^2$ independently represents a linear, branched or cyclic alkyl group having 1 to 10 carbon atoms, an aryl group having 6 to 10 carbon atoms, an alkenyl group having 2 to 10 carbon atoms, or a hydroxyl group, provided that at least one $R^2$ represents a hydroxyl group, each m is independently an integer of 1 to 4, n is an integer of 1 to 4, and p is 0 or 1.)

[2] A material for forming an underlayer film for lithography, comprising the compound according to [1].

[3] The material for forming the underlayer film for lithography according to [2], wherein the compound represented by the general formula (1) comprises at least one of compounds represented by the following general formula (1a) and general formula (1b).

[Formula 2]

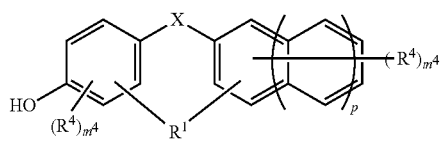

(1 a)

-continued

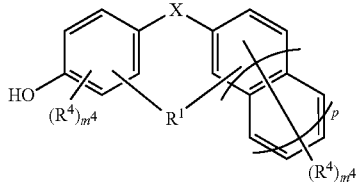

(1 b)

(in formula (1a) and (1b), X represents an oxygen atom or a sulfur atom, $R^1$ represents a single bond or a 2-valent hydrocarbon group having 1 to 30 carbon atoms, the hydrocarbon group may have a cyclic hydrocarbon group, a double bond, a hetero atom or an aromatic group having 6 to 30 carbon atoms, each $R^4$ independently represents a linear, branched or cyclic alkyl group having 1 to 10 carbon atoms, an aryl group having 6 to 10 carbon atoms, an alkenyl group having 2 to 10 carbon atoms, or a hydroxyl group, each $m^4$ is independently an integer of 0 to 3, and p is 0 or 1.)

[4] A material for forming an underlayer film for lithography, containing a resin having a structure represented by the following general formula (2).

[Formula 3]

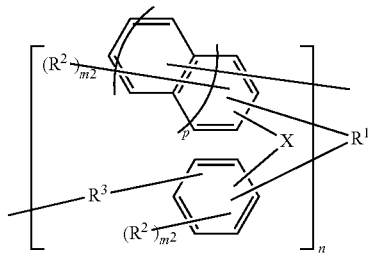

(2)

(in formula (2), each X independently represents an oxygen atom or a sulfur atom, $R^1$ represents a single bond or a 2n-valent hydrocarbon group having 1 to 30 carbon atoms, the hydrocarbon group may have a cyclic hydrocarbon group, a double bond, a hetero atom or an aromatic group having 6 to 30 carbon atoms, and each $R^2$ independently represents a linear, branched or cyclic alkyl group having 1 to 10 carbon atoms, an aryl group having 6 to 10 carbon atoms, an alkenyl group having 2 to 10 carbon atoms, or a hydroxyl group, provided that at least one $R^2$ represents a hydroxyl group, each $R^3$ independently represents a single bond, or a linear or branched alkylene group having 1 to 20 carbon atoms, each $m^2$ is independently an integer of 1 to 3, n is an integer of 1 to 4, and p is 0 or 1.)

[5] The material for forming the underlayer film for lithography according to any of [2] to [4], further containing an organic solvent.

[6] The material for forming the underlayer film for lithography according to any of [2] to [5], further containing an acid generating agent.

[7] The material for forming the underlayer film for lithography according to any of [2] to [6], further containing a crosslinking agent.

[8] An underlayer film for lithography, formed from the material for forming the underlayer film for lithography according to any of [2] to [7].

[9] A pattern forming method, comprising:
step (A-1) of forming an underlayer film on a substrate by using the material for forming the underlayer film according to any of [2] to [7];
step (A-2) of forming at least one photoresist layer on the underlayer film; and
step (A-3) of irradiating a predetermined region of the photoresist layer with radiation followed by developing with an alkali, after step (A-2).

[10] A pattern forming method, comprising:
step (B-1) of forming an underlayer film on a substrate by using the material for forming the underlayer film according to any of [2] to [7];
step (B-2) of forming an intermediate layer film on the underlayer film by using a silicon atom-containing resist intermediate layer film material;
step (B-3) of forming at least one photoresist layer on the intermediate layer film;
step (B-4) of irradiating a predetermined region of the photoresist layer with radiation followed by developing with an alkali to form a resist pattern, after step (B-3); and
step (B-5) of etching the intermediate layer film while the resist pattern functions as a mask, etching the underlayer film while the obtained intermediate layer film pattern functions as an etching mask and etching the substrate while the obtained underlayer film pattern functions as an etching mask to form a pattern on the substrate, after step (B-4).

According to the present invention, it is possible to provide a material for forming an underlayer film for lithography, which can be applied to a wet process and which is useful for forming a photoresist underlayer film excellent in heat resistance and etching resistance.

DESCRIPTION OF EMBODIMENTS

Hereinafter, embodiments of the present invention (hereinafter, also simply designated as "the present embodiment") will be described. It is to be noted that the following embodiments are illustrative for describing the present invention, and the present invention is not limited only to the embodiments.

(Compound and Material for Forming Underlayer Film for Lithography)

A compound of the present embodiment is represented by the following general formula (1). The compound of the present embodiment has such a structure, and therefore has a high heat resistance, a relatively high carbon concentration, a relatively low oxygen concentration, and also a high solvent solubility. Moreover, a material for forming an underlayer film for lithography of the present embodiment contains at least the compound of the present embodiment. The material for forming an underlayer film for lithography of the present embodiment has such a structure, and therefore can be applied to a wet process, and is excellent in heat resistance and etching resistance. Furthermore, the material for forming an underlayer film for lithography of the present embodiment is formed using the above compound or resin, and therefore the material can be used to form an underlayer film whose degradation is suppressed at high-temperature baking and which is also excellent in etching resistance to oxygen plasma etching or the like. Moreover, the material for forming an underlayer film for lithography of the present embodiment is also excellent in adhesiveness with a resist layer, and therefore can provide an excellent resist pattern.

[Formula 4]

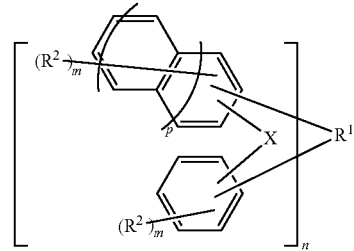

In the formula (1), each X independently represents an oxygen atom or a sulfur atom, and respective benzene rings are bonded with each other via X. $R^1$ represents a single bond or a 2n-valent hydrocarbon group having 1 to 30 carbon atoms, and respective benzene rings are bonded with each other via $R^1$. Herein, the 2n-valent hydrocarbon group may have a cyclic hydrocarbon group, a double bond, a hetero atom or an aromatic group having 6 to 30 carbon atoms. Each $R^2$ independently represents a monovalent substituent selected from the group consisting of a linear, branched or cyclic alkyl group having 1 to 10 carbon atoms, an aryl group having 6 to 10 carbon atoms, an alkenyl group having 2 to 10 carbon atoms and a hydroxyl group, and m number of $R^2$(s) is bonded to each benzene ring. Herein, at least one $R^2$ represents a hydroxyl group. In addition, each m is independently an integer of 1 to 4, p is 0 or 1, and n is an integer of 1 to 4.

Herein, the 2n-valent hydrocarbon group represents an alkylene group having 1 to 30 carbon atoms when n=1, an alkanetetrayl group having 1 to 30 carbon atoms when n=2, an alkanehexayl group having 2 to 30 carbon atoms when n=3, and an alkaneoctayl group having 3 to 30 carbon atoms when n=4. Examples of the 2n-valent hydrocarbon group include those having a linear, branched or cyclic structure.

In addition, the 2n-valent hydrocarbon group may have a cyclic hydrocarbon group, a double bond, a hetero atom, or an aromatic group having 6 to 30 carbon atoms. Herein, the cyclic hydrocarbon group also includes a bridged cyclic hydrocarbon group.

The compound represented by general formula (1) has a high heat resistance due to rigidity of its structure while having a low molecular weight, as compared with a conventional resist underlayer film material including a polymer formed by co-polymerizing a repeating unit of acenaphthylene with a substituted or non-substituted repeating unit having a hydroxy group, and therefore the compound can be used even under a high-temperature baking condition. In addition, the compound represented by general formula (1) has a low molecular weight and a low viscosity as compared with the above conventional resist underlayer film material and the like, and therefore even when being applied to a substrate having a step (in particular, fine space, hole pattern and the like), the compound can be easily filled uniformly in every part of the step, and as a result, a material for forming an underlayer film for lithography using such a compound can be improved in terms of embedding properties in an advantageous manner as compared with the above conventional resist underlayer film material and the like. In addition, the compound has a relatively high carbon concentration to thereby impart also a high etching resistance.

Herein, the compound represented by the general formula (1) is preferably a compound represented by the following formula (1-0).

[Formula 5]

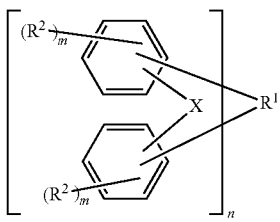

(1-0)

(In the formula (1-0), $R^1$, $R^2$, m, n, and X are the same as defined in the formula (1).)

In addition, the compound represented by the general formula (1-0) is more preferably a compound represented by the following formula (1-1).

[Formula 6]

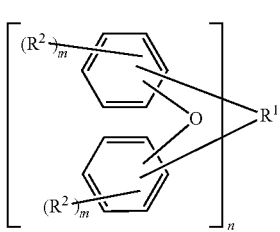

(1-1)

(In the formula (1-1), $R^1$, $R^2$, m, and n are the same as defined in the formula (1).)

In addition, the compound represented by the general formula (1-1) is further preferably a compound represented by the following formula (1-2).

[Formula 7]

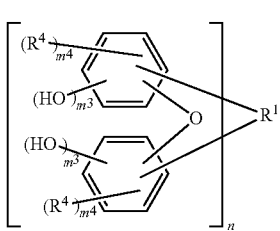

(1-2)

(In the formula (1-2), $R^1$ and n are the same as defined in the formula (1), $R^4$ is the same as $R^2$ in the formula (1), each $m^3$ is independently an integer of 1 to 4, each $m^4$ is independently an integer of 0 to 3, and $m^3+m^4$ is an integer of 1 to 4.)

The compound represented by the general formula (1-2) is particularly preferably a compound represented by the following formula (1-3).

[Formula 8]

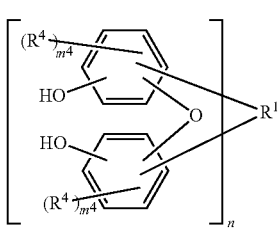

(1-3)

(In the formula (1-3), $R^1$, $R^4$, and $m^4$ are the same as defined in the formula (1-2).)

In addition, the compound represented by the general formula (1) is preferably a mode where n=1 in the formula (1), namely, preferably includes at least one of compounds represented by the following general formula (1a) and general formula (1b), in terms of having a low molecular weight.

[Formula 9]

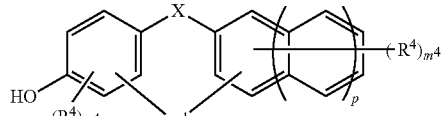

(1 a)

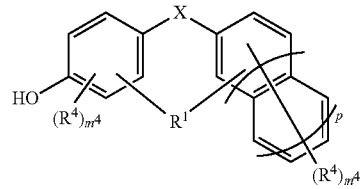

(1 b)

In the formula (1a) and the formula (1b), X, $R^1$, and p are the same as defined in the formula (1), and $R^4$ and $m^4$ are the same as defined in the formula (1-2).

Furthermore, the compound represented by the general formula (1a) is more preferably a mode where p=0 in the formula (1a), namely, more preferably includes a compound represented by the following formula (1c).

[Formula 10]

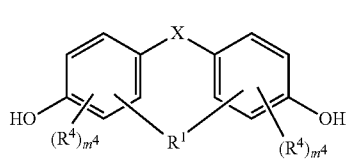

(1 c)

In the formula (1c), X and $R^1$ are the same as defined in the formula (1), and $R^4$ and $m^4$ are the same as defined in the formula (1-2).

Furthermore, the compound represented by the general formula (1c) is particularly preferably a mode where X represents an oxygen atom (O) in the formula (1c), namely, particularly preferably includes a compound represented by the following formula (1-4).

[Formula 11]

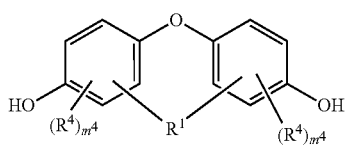

(1-4)

(In the formula (1-4), $R^1$, $R^4$, and $m^4$ are the same as defined in the formula (1a).)

Specific examples of the compound represented by the general formula (1) include the following, but not limited to those recited herein.

[Formula 12]
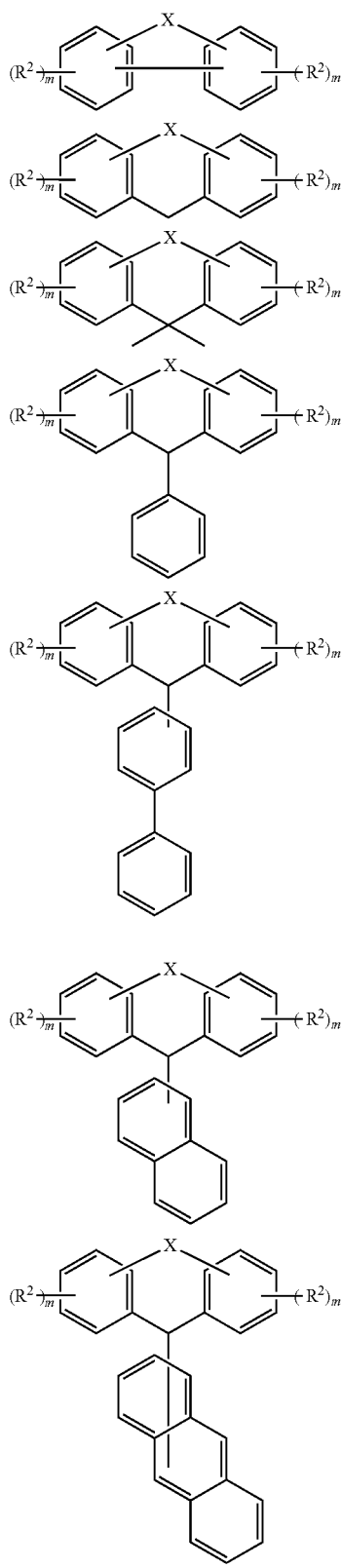
(wherein R², X, and m are the same as defined in the formula (1).)
[Formula 13]
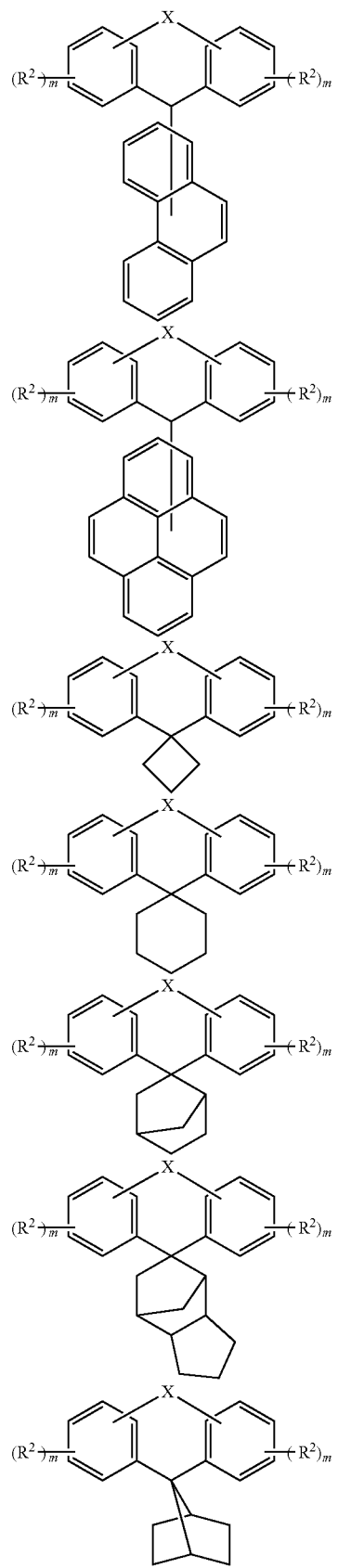

-continued
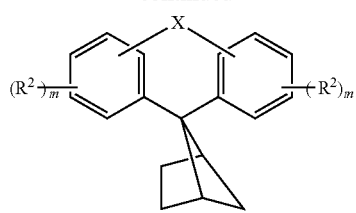
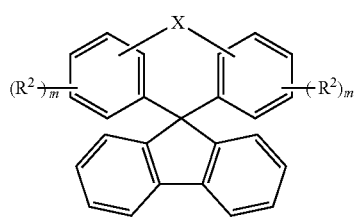
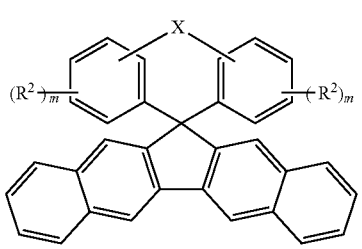
(wherein $R^2$, X, and m are the same as defined in the formula (1).)
[Formula 14]
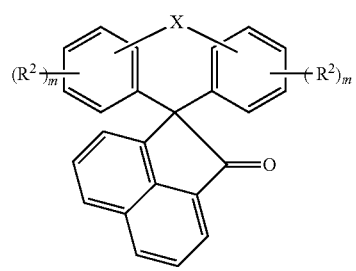
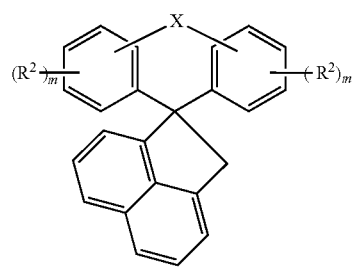
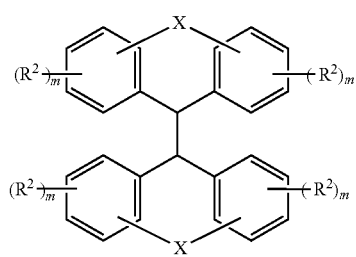
-continued
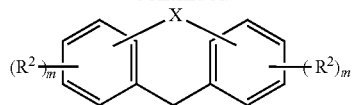
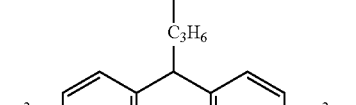
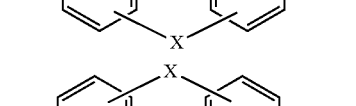
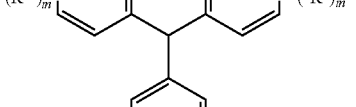
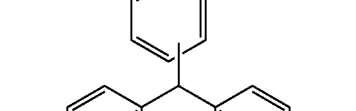
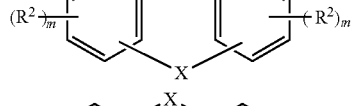
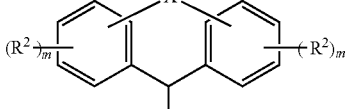
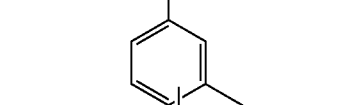
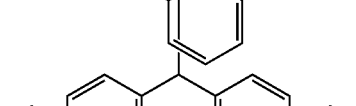
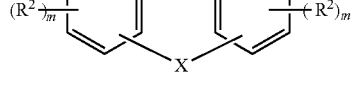
(wherein $R^2$, X, and m are the same as defined in the formula (1).)
[Formula 15]
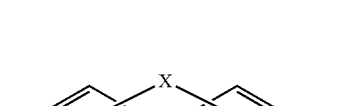
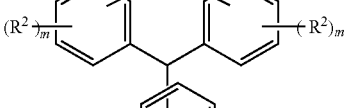
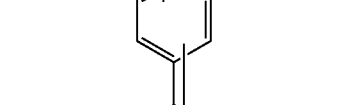
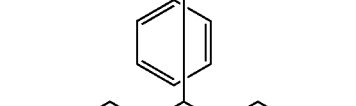
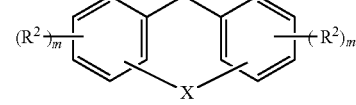

-continued
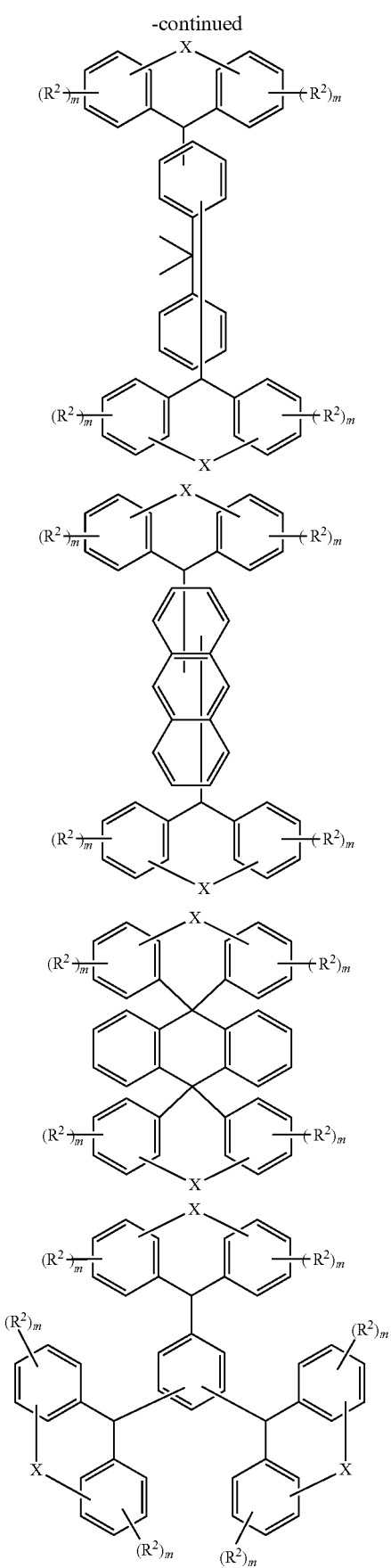
(wherein $R^2$, X, and m are the same as defined in the formula (1).)
Specific examples of the compound represented by the general formula (1) further include the following, but not limited to those recited herein.
[Formula 16]
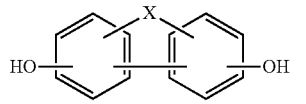
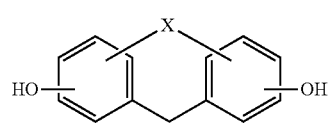
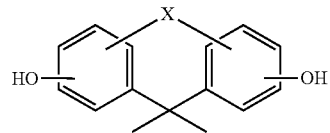
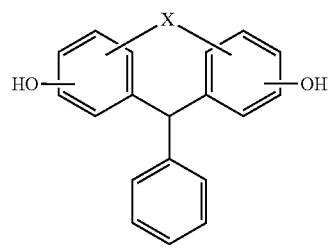
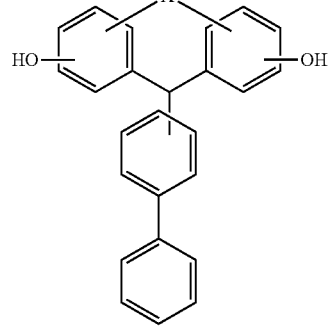
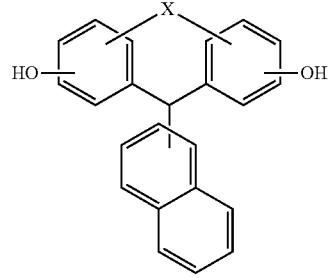

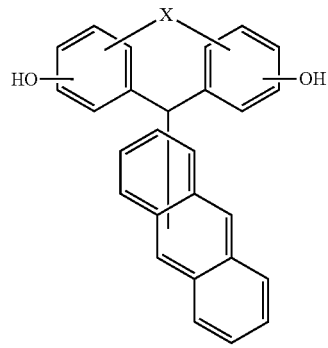
(wherein X is the same as defined in the formula (1).)
[Formula 17]
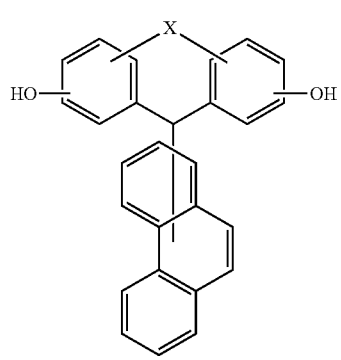
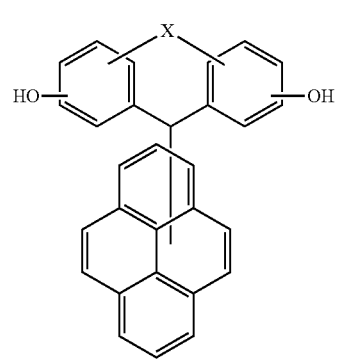
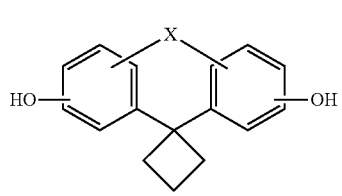
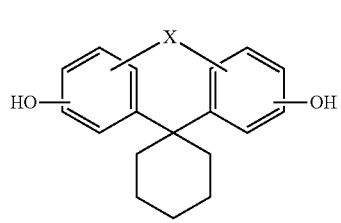
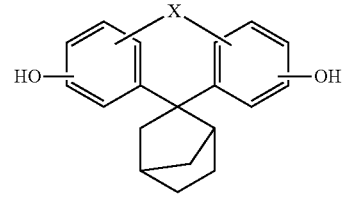
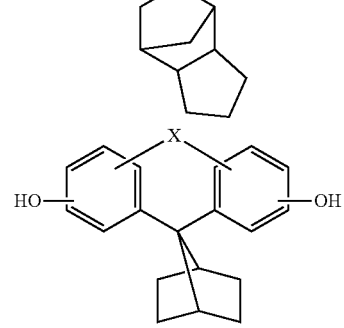
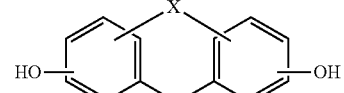
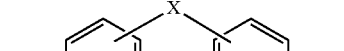
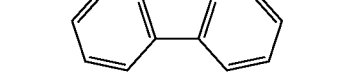
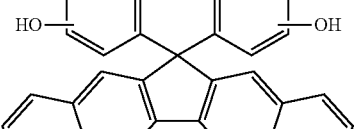
(wherein X is the same as defined in the formula (1).)
[Formula 18]
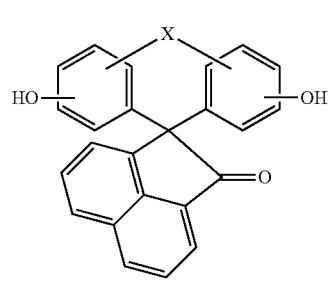

-continued
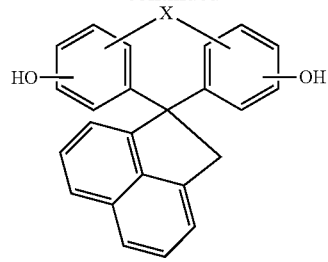
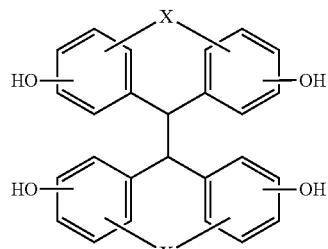
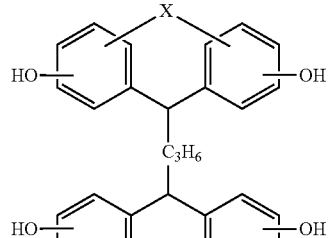
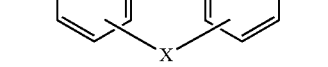
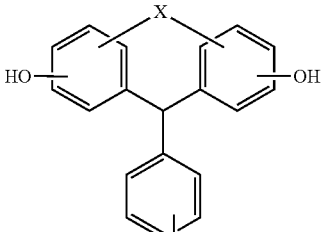
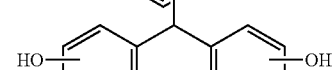
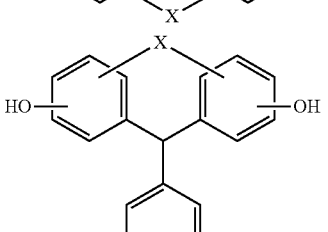
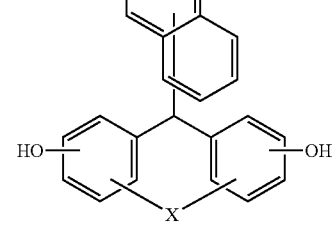
(wherein X is the same as defined in the formula (1).)
[Formula 19]
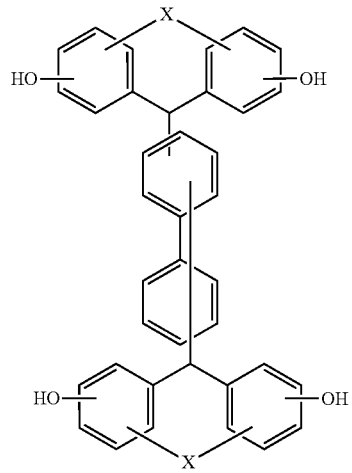
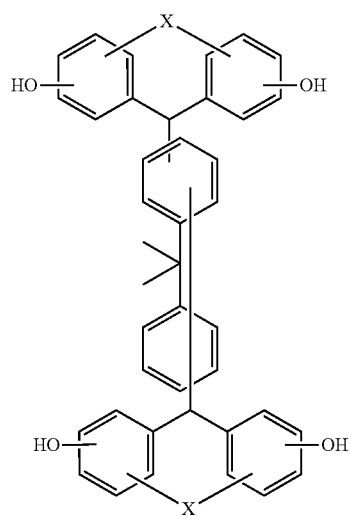
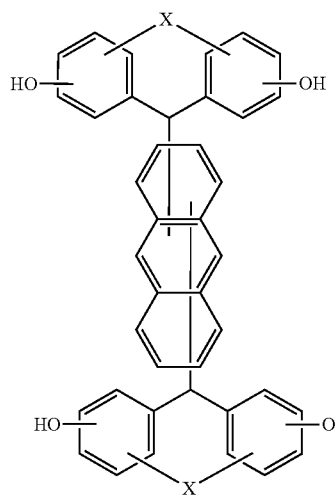

-continued

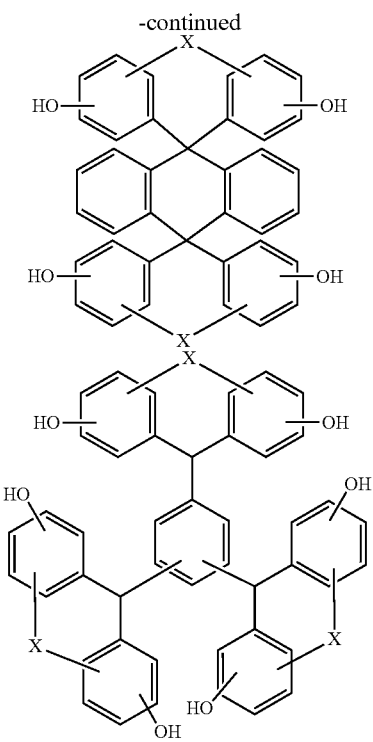

(wherein X is the same as defined in the formula (1).)

The compound represented by the general formula (1) can be appropriately synthesized by applying a known method, and a synthesis method thereof is not particularly limited. For example, phenols or thiophenols, and aldehydes or ketones corresponding to a desired compound structure can be subjected to a polycondensation reaction under ordinary pressure in the presence of an acid catalyst to thereby provide the compound represented by the general formula (1) where p=0. The compound represented by the general formula (1) where p=1 can be synthesized in the same manner by using the phenols or thiophenols in combination with naphthols or thionaphthols. The reaction can also be performed under pressure, if necessary.

Examples of the phenols include phenol, methylphenol, methoxybenzene, catechol, resorcinol, hydroquinone, and trimethylhydroquinone, but are not particularly limited thereto. These can be used alone, or two or more thereof can be used in combination. Among them, hydroquinone or trimethylhydroquinone is more preferably used from the viewpoint of being capable of easily making a xanthene structure.

Examples of the thiophenols include benzenethiol, methylbenzenethiol, methoxybenzenethiol, benzenedithiol, and trimethylbenzenedithiol, but are not particularly limited thereto. These can be used alone, or two or more thereof can be used in combination. Among them, benzenedithiol or trimethylbenzenedithiol is more preferably used from the viewpoint of being capable of easily making a thioxanthene structure.

Examples of the naphthols include naphthol, methylnaphthol, methoxynaphthalene, naphthalenediol, and naphthalenetriol but are not particularly limited thereto. These can be used alone, or two or more thereof can be used in combination. Among them, naphthalenediol or naphthalenetriol is more preferably used from the viewpoint of being capable of easily making a xanthene structure.

Examples of the thionaphthols include naphthalenethiol, methylnaphthalenethiol, methoxy naphthalenethiol, naphthalenedithiol and naphthalenetrithiol, but are not particularly limited thereto. These can be used alone, or two or more thereof can be used in combination. Among them, naphthalenedithiol or naphthalenetrithiol is more preferably used from the viewpoint of being capable of easily making a thioxanthene structure.

Examples of the aldehydes include formaldehyde, trioxane, paraformaldehyde, acetaldehyde, propylaldehyde, butylaldehyde, hexylaldehyde, decylaldehyde, undecylaldehyde, phenylacetaldehyde, phenylpropylaldehyde, furfural, benzaldehyde, hydroxybenzaldehyde, fluorobenzaldehyde, chlorobenzaldehyde, nitrobenzaldehyde, methylbenzaldehyde, dimethylbenzaldehyde, ethylbenzaldehyde, propylbenzaldehyde, butylbenzaldehyde, cyclohexylbenzaldehyde, biphenylaldehyde, naphthaldehyde, anthracenecarboxaldehyde, phenanthrenecarboxaldehyde, pyrenecarboxaldehyde, glyoxal, glutaraldehyde, phthalaldehyde, naphthalenedicarboxaldehyde, biphenyldicarboxaldehyde, anthracenedicarboxaldehyde, bis(diformylphenyl)methane, bis(diformylphenyl)propane, and benzenetricarboxaldehyde, but are not particularly limited thereto. These can be used alone, or two or more thereof can be used in combination. Among them, benzaldehyde, hydroxybenzaldehyde, fluorobenzaldehyde, chlorobenzaldehyde, nitrobenzaldehyde, methylbenzaldehyde, dimethylbenzaldehyde, ethylbenzaldehyde, propylbenzaldehyde, butylbenzaldehyde, cyclohexylbenzaldehyde, biphenylaldehyde, naphthaldehyde, anthracenecarboxaldehyde, phenanthrenecarboxaldehyde, pyrenecarboxaldehyde, glyoxal, glutaraldehyde, phthalaldehyde, naphthalenedicarboxaldehyde, biphenyldicarboxaldehyde, anthracenedicarboxaldehyde, bis(diformylphenyl)methane, bis(diformylphenyl)propane, or benzenetricarboxaldehyde is preferably used from the viewpoint of imparting a high heat resistance.

Examples of the ketones include acetone, methyl ethyl ketone, cyclobutanone, cyclopentanone, cyclohexanone, norbornanone, tricyclohexanone, tricyclodecanone, adamantanone, fluorenone, benzofluorenone, acenaphthenequinone, acenaphthenone, and anthraquinone, but are not particularly limited thereto. These can be used alone, or two or more thereof can be used in combination. Among them, cyclopentanone, cyclohexanone, norbornanone, tricyclohexanone, tricyclodecanone, adamantanone, fluorenone, benzofluorenone, acenaphthenequinone, acenaphthenone, or anthraquinone is preferably used from the viewpoint of imparting a high heat resistance.

The acid catalyst for use in the above reaction can be appropriately selected from known ones and used, and is not particularly limited. Such an acid catalyst is an inorganic acid or an organic acid, as widely known. Specific examples of the acid catalyst include inorganic acids such as hydrochloric acid, sulfuric acid, phosphoric acid, hydrobromic acid, and hydrofluoric acid; organic acids such as oxalic acid, malonic acid, succinic acid, adipic acid, sebacic acid, citric acid, fumaric acid, maleic acid, formic acid, p-toluenesulfonic acid, methanesulfonic acid, trifluoroacetic acid, dichloroacetic acid, trichloroacetic acid, trifluoromethanesulfonic acid, benzenesulfonic acid, naphthalenesulfonic acid, and naphthalenedisulfonic acid; Lewis acids such as zinc chloride, aluminum chloride, iron chloride, and boron trifluoride; and solid acids such as tungstosilicic acid, tungstophosphoric acid, silicomolybdic acid, and phosphomolybdic acid, but are not particularly limited thereto. Among them, organic acids and solid acids are preferable in terms of production, and hydrochloric acid or sulfuric acid is preferably used in terms of production such as availability or handleability. Herein, these acid catalysts can be used alone, or two or more thereof can be used in combination. In addition, the amount of the acid catalyst to be used can be appropriately set depending on the types of raw materials to be used and the catalyst to be used, reaction conditions, and the like, and is not particularly limited, but the amount is preferably 0.01 to 100 parts by mass based on 100 parts by mass of reaction raw materials.

A reaction solvent may also be used during the above reaction. The reaction solvent that can be used is not particularly limited and is appropriately selected from known ones as long as the reaction of the aldehydes or ketones to be used and the phenols or thiophenols to be used progresses. Examples thereof include water, methanol, ethanol, propanol, butanol, tetrahydrofuran, dioxane, ethylene glycol dimethyl ether, ethylene glycol diethyl ether, or a mixed solvent thereof. Herein, these solvents can be used alone, or two or more thereof can be used in combination. In addition, the amount of the solvent to be used can be appropriately set depending on the types of raw materials to be used and the acid catalyst to be used, reaction conditions, and the like. The amount of the solvent to be used is not particularly limited, and is preferably in the range from 0 to 2000 parts by mass based on 100 parts by mass of reaction raw materials. Furthermore, the reaction temperature in the above reaction can be appropriately selected depending on the reactivity of reaction raw materials. The reaction temperature is not particularly limited, and is usually preferably in the range from 10 to 200° C. In order to form a xanthene structure or a thioxanthene structure as the compound represented by general formula (1) of the present embodiment, the reaction temperature is preferably high and, specifically, preferably ranges from 60 to 200° C. Herein, the reaction method that can be used is appropriately selected from known methods, and is not particularly limited, but includes a method in which the phenols or thiophenols, the aldehydes or ketones, and the acid catalyst are charged at once, and a method in which the phenols or thiophenols and the aldehydes or ketones are dropped in the presence of the acid catalyst. After completion of the polycondensation reaction, the resulting compound can be isolated according to an ordinary method, and the isolation method is not particularly limited. For example, in order to remove the unreacted raw materials and the acid catalyst present in the system, a common method in which the temperature in a reaction tank is raised to 130 to 230° C. to remove a volatile content at about 1 to 50 mmHg can be adopted to thereby provide an objective compound.

The reaction progresses under such a preferable reaction condition that 1 mol to an excess amount of the phenols or thiophenols and 0.001 to 1 mol of the acid catalyst are used, based on 1 mol of the aldehydes or ketones and are reacted at ordinary pressure and at 50 to 150° C. for about 20 minutes to 100 hours.

After completion of the reaction, the objective compound can be isolated by a known method. For example, the objective compound, the compound represented by the general formula (1), can be obtained by concentrating a reaction liquid, adding pure water thereto to precipitate a reaction product, cooling the resultant to room temperature followed by filtration for separation, drying a solid obtained by filtration, then separating the solid into the reaction product and a by-product for purification by column chromatography, and performing distilling off of the solvent, filtration and drying.

The molecular weight of the compound represented by the general formula (1) is not particularly limited, but the weight average molecular weight Mw thereof is preferably 350 to 5,000, and more preferably 400 to 3,000. Herein, the Mw can be measured by a method described in Examples described later.

The compound represented by the general formula (1) can be used as a material for forming an underlayer film for lithography, as it is. In addition, the compound can also be used as an oligomeric resin obtained by reacting the compound with a monomer having crosslinking reactivity. Examples of the oligomeric resin obtained from the compound represented by the general formula (1) include those having a structure represented by the following general formula (2). That is, the material for forming an underlayer film for lithography according to the present embodiment may be one at least containing a resin having a structure represented by the following general formula (2).

[Formula 20]

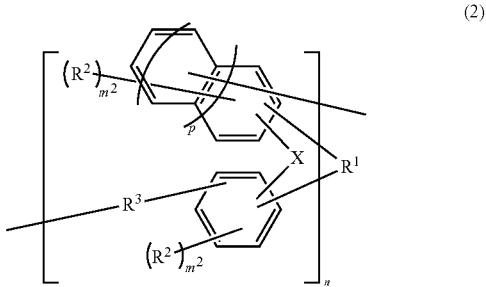

(2)

In the formula (2), each X independently represents an oxygen atom or a sulfur atom. $R^1$ represents a single bond or a 2n-valent hydrocarbon group having 1 to 30 carbon atoms, and the hydrocarbon group may have a cyclic hydrocarbon group, a double bond, a hetero atom or an aromatic group having 6 to 30 carbon atoms. Each $R^2$ independently represents a linear, branched or cyclic alkyl group having 1 to 10 carbon atoms, an aryl group having 6 to 10 carbon atoms, an alkenyl group having 2 to 10 carbon atoms, or a hydroxyl group, provided that at least one $R^2$ represents a hydroxyl group. Each $R^3$ independently represents a single bond, or a linear or branched alkylene group having 1 to 20 carbon atoms. Each $m^2$ is independently an integer of 1 to 3, n is an integer of 1 to 4, and p is 0 or 1. Herein, the 2n-valent hydrocarbon group is the same as defined in the formula (1).

The monomer having crosslinking reactivity that can be used is known one without particular limitation as long as the one enables to form an oligomer of the compound represented by the general formula (1). Specific examples thereof include aldehyde, ketone, carboxylic acid, carboxylic halide, a halogen-containing compound, an amino compound, an imino compound, isocyanate, and an unsaturated hydrocarbon group-containing compound, but are not particularly limited thereto.

A monomer having crosslinking reactivity with an aromatic ring contained in $R^1$ in the formula (2) may be reacted as long as a desired object of the present embodiment is not impaired.

Specific examples of the resin having a structure represented by general formula (2) include a novolac resin obtained by a condensation reaction of the compound represented by the general formula (1) with an aldehyde as the monomer having crosslinking reactivity, or the like.

Herein, examples of the aldehyde for use in forming the novolac resin of the compound represented by the general formula (1) include formaldehyde, trioxane, paraformaldehyde, benzaldehyde, acetaldehyde, propylaldehyde, phenylacetaldehyde, phenylpropylaldehyde, hydroxybenzaldehyde, chlorobenzaldehyde, nitrobenzaldehyde, methylbenzaldehyde, ethylbenzaldehyde, butylbenzaldehyde, biphenylaldehyde, naphthaldehyde, anthracenecarbaldehyde, phenanthrenecarbaldehyde, pyrenecarbaldehyde, and furfural, but are not particularly limited thereto. Among them, formaldehyde is more preferable. Herein, these aldehydes can be used alone, or two or more thereof can be used in combination. In addition, the amount of the aldehydes to be used is not particularly limited, but the amount is preferably 0.2 to 5 mol and more preferably 0.5 to 2 mol, based on 1 mol of the compound represented by the general formula (1).

A acid catalyst can also be used in the condensation reaction of the compound represented by the general formula (1) with an aldehyde. The acid catalyst that can be here used is appropriately selected from known ones, and is not particularly limited. Such an acid catalyst is an inorganic acid or an organic acid, as widely known. Specific examples of the acid catalyst include inorganic acids such as hydrochloric acid, sulfuric acid, phosphoric acid, hydrobromic acid, or hydrofluoric acid; organic acids such as oxalic acid, malonic acid, succinic acid, adipic acid, sebacic acid, citric acid, fumaric acid, maleic acid, formic acid, p-toluenesulfonic acid, methanesulfonic acid, trifluoroacetic acid, dichloroacetic acid, trichloroacetic acid, trifluoromethanesulfonic acid, benzenesulfonic acid, naphthalenesulfonic acid, or naphthalenedisulfonic acid; Lewis acids such as zinc chloride, aluminum chloride, iron chloride, or boron trifluoride; or solid acids such as tungstosilicic acid, tungstophosphoric acid, silicomolybdic acid, or phosphomolybdic acid, but are not particularly limited thereto. Among them, organic acids and solid acids are preferable in terms of production, and hydrochloric acid or sulfuric acid is preferably used in terms of production such as availability or handleability. Herein, these acid catalysts can be used alone, or two or more thereof can be used in combination. In addition, the amount of the acid catalyst to be used can be appropriately set depending on the types of raw materials to be used and the catalyst to be used, reaction conditions, and the like, and is not particularly limited, but the amount is preferably 0.01 to 100 parts by mass based on 100 parts by mass of reaction raw materials. However, in the case of copolymerization with a compound having a non-conjugated double bond, such as indene, hydroxyindene, benzofuran, hydroxyanthracene, acenaphthylene, biphenyl, bisphenol, trisphenol, dicyclopentadiene, tetrahydroindene, 4-vinylcyclohexene, norbornadiene, 5-vinylnorborna-2-ene, α-pinene, β-pinene, and limonene, the aldehydes are not necessarily required.

A reaction solvent can also be used in the condensation reaction of the compound represented by the general formula (1) with an aldehyde. The reaction solvent in the polycondensation, which can be used, is appropriately selected from known ones, and is not particularly limited, but examples thereof include water, methanol, ethanol, propanol, butanol, tetrahydrofuran, dioxane, or a mixed solvent thereof. Herein, these solvents can be used alone, or two or more thereof can be used in combination. In addition, the amount of the solvent to be used can be appropriately set depending on the types of raw materials to be used and the acid catalyst to be used, reaction conditions, and the like, and is not particularly limited, but the amount preferably ranges from 0 to 2000 parts by mass based on 100 parts by mass of reaction raw materials. Furthermore, the reaction temperature can be appropriately selected depending on the reactivity of reaction raw materials, and is not particularly limited, but the reaction temperature usually ranges from 10 to 200° C. Herein, the reaction method that can be used is appropriately selected from known methods, and is not particularly limited, but includes a method in which the compound represented by the general formula (1), the aldehydes, and the acid catalyst are charged at once, and a method in which the compound represented by the general formula (1) and the aldehydes are dropped in the presence of the acid catalyst. After completion of the polycondensation reaction, the resulting compound can be isolated according to an ordinary method, and the isolation method is not particularly limited. For example, in order to remove the unreacted raw materials and the acid catalyst present in the system, a common method in which the temperature in a reaction tank is raised to 130 to 230° C. to remove a volatile content at about 1 to 50 mmHg can be adopted to thereby provide an objective novolac resin.

Herein, the resin having a structure represented by the general formula (2) may be a homopolymer of the compound represented by the general formula (1), or may be a copolymer thereof with other phenols. Examples of the copolymerizable phenols include phenol, cresol, dimethylphenol, trimethylphenol, butylphenol, phenylphenol, diphenylphenol, naphthylphenol, resorcinol, methylresorcinol, catechol, butylcatechol, methoxyphenol, methoxyphenol, propylphenol, pyrogallol, and thymol, but are not particularly limited thereto.

In addition, the resin having a structure represented by the general formula (2) may be one obtained by copolymerization with a polymerizable monomer other than the above-described other phenols. Examples of such a copolymerizable monomer include naphthol, methylnaphthol, methoxynaphthol, dihydroxynaphthalene, indene, hydroxyindene, benzofuran, hydroxyanthracene, acenaphthylene, biphenyl, bisphenol, trisphenol, dicyclopentadiene, tetrahydroindene, 4-vinylcyclohexene, norbornadiene, vinylnorbornaene, pinene, and limonene, but are not particularly limited thereto. Herein, the resin having a structure represented by the general formula (2) may be a bi or higher functional (for example, bi to tetra) copolymer of the compound represented by the general formula (1) with phenols, a bi or higher functional (for example, bi to tetra) copolymer of the compound represented by the general formula (1) with the above-described copolymerizable monomer, or a ter or higher (for example, ter to tetra) copolymer of the compound represented by the general formula (1), the above-described phenols, and the above-described copolymerizable monomer.

Herein, the molecular weight of the resin having a structure represented by the general formula (2) is not particularly limited, and the weight average molecular weight (Mw) in terms of polystyrene is preferably 500 to 30,000, and more preferably 750 to 20,000. In addition, the resin having a structure represented by the general formula (2) preferably has a dispersity (weight average molecular weight Mw/number average molecular weight Mn) in a range from 1.2 to 7 from the viewpoints of improving a crosslinking efficiency and suppressing a volatile component during baking. Herein, the Mn can be determined by a method described in Examples described later.

The compound represented by general formula (1) and/or the resin having a structure represented by the general formula (2) preferably have/has a high solubility in the solvent from the viewpoint of making the application of a wet process easier. More specifically, such a compound and/or resin preferably have/has a solubility of 10% by mass or more in a solvent when the solvent is 1-methoxy-2-propanol (PGME) and/or propylene glycol monomethyl ether acetate (PGMEA). Herein, the solubility in PGME and/or PGMEA is defined as "Mass of resin/(Mass of resin+Mass of solvent)×100 (% by mass)". For example, when 10 g of a compound represented by the general formula (1) and/or a resin having a structure represented by the general formula (2) is dissolved in 90 g of PGMEA, the solubility of the compound represented by general formula (1) and/or the resin having a structure represented by the general formula (2) in PGMEA is evaluated as being "10% by mass or more", and when not dissolved, the solubility is evaluated as being "less than 10% by mass".

In the case where the material for forming an underlayer film for lithography according to the present embodiment contains an organic solvent that is an optional component described later, the contents of the compound represented by general formula (1) and the resin having a structure represented by the general formula (2) are not particularly limited, but the contents are preferably 1 to 33 parts by mass, more preferably 2 to 25 parts by mass, and further preferably 3 to 20 parts by mass, based on 100 parts by mass of the total amount of the components including the organic solvent.

(Other Component)

The material for forming an underlayer film for lithography according to the present embodiment may contain, if necessary, other component such as a crosslinking agent, an acid generating agent, and an organic solvent, other than the compound represented by general formula (1) and/or the resin having a structure represented by the general formula (2). Hereinafter, these optional components will be described.

The material for forming an underlayer film for lithography according to the present embodiment may contain, if necessary, a crosslinking agent from the viewpoint of suppressing intermixing and the like.

Specific examples of the crosslinking agent usable in the present embodiment include a melamine compound, a guanamine compound, a glycoluril compound, a urea compound, an epoxy compound, a thioepoxy compound, an isocyanate compound, an azide compound, and a compound including a double bond such as an alkenyl ether group, these compounds having, as a substituent (crosslinkable group), at least one group selected from a methylol group, an alkoxymethyl group, and an acyloxymethyl group, but are not particularly limited thereto. Herein, these crosslinking agents can be used alone, or two or more thereof can be used in combination. Such a crosslinking agent may also be used as an additive. Herein, the crosslinkable group may also be introduced as a pendant group into a polymer side chain in the compound represented by general formula (1) and/or the resin having a structure represented by the general formula (2). A compound including a hydroxy group can also be used as the crosslinking agent.

Specific examples of the melamine compound include, for example, hexamethylolmelamine, hexamethoxymethylmelamine, a compound in which 1 to 6 methylol groups in hexamethylolmelamine are methoxymethylated, or mixtures thereof, and hexamethoxyethylmelamine, hexaacyloxymethylmelamine, a compound in which 1 to 6 methylol groups in hexamethylolmelamine are acyloxymethylated, or mixtures thereof. Specific examples of the epoxy compound include, for example, tris(2,3-epoxypropyl)isocyanurate, trimethylolmethane triglycidyl ether, trimethylolpropane triglycidyl ether, and triethylolethane triglycidyl ether.

Specific examples of the guanamine compound include, for example, tetramethylolguanamine, tetramethoxymethylguanamine, a compound in which 1 to 4 methylol groups in tetramethylolguanamine are methoxymethylated, or mixtures thereof, and tetramethoxyethylguanamine, tetraacyloxyguanamine, a compound in which 1 to 4 methylol groups in tetramethylolguanamine are acyloxymethylated, or mixtures thereof. Specific examples of the glycoluril compound include, for example, tetramethylolglycoluril, tetramethoxyglycoluril, tetramethoxymethylglycoluril, a compound in which 1 to 4 methylol groups in tetramethylolglycoluril are methoxymethylated, or mixtures thereof, and a compound in which 1 to 4 methylol groups in tetramethylolglycoluril are acyloxymethylated, or mixtures thereof. Specific examples of the urea compound include, for example, tetramethylolurea, tetramethoxymethylurea, a compound in which 1 to 4 methylol groups in tetramethylolurea are methoxymethylated, or mixtures thereof, and tetramethoxyethylurea.

Specific examples of the compound including an alkenyl ether group include, for example, ethylene glycol divinyl ether, triethylene glycol divinyl ether, 1,2-propanediol divinyl ether, 1,4-butanediol divinyl ether, tetramethylene glycol divinyl ether, neopentyl glycol divinyl ether, trimethylolpropane trivinyl ether, hexanediol divinyl ether, 1,4-cyclohexanediol divinyl ether, pentaerythritol trivinyl ether, pentaerythritol tetravinyl ether, sorbitol tetravinyl ether, sorbitol pentavinyl ether, and trimethylolpropane trivinyl ether.

In the material for forming an underlayer film for lithography according to the present embodiment, the content of the crosslinking agent is not particularly limited, but the content is preferably 5 to 50 parts by mass and more preferably 10 to 40 parts by mass, based on 100 parts by mass of the compound represented by the general formula (1) and the resin having a structure represented by the general formula (2). The content is set within the above preferable range to result in tendencies to suppress the occurrence of the mixing phenomenon with the resist layer, and to result in tendencies to enhance an antireflective effect and improve film formability after crosslinking.

The material for forming an underlayer film for lithography of the present embodiment may also contain, if necessary, an acid generating agent from the viewpoint of further promoting a crosslinking reaction by heat. As the acid generating agent, one for generating an acid by pyrolysis and one for generating an acid by light irradiation are known, and any of them can be used.

The acid generating agent includes:
1) an onium salt of the following general formula (P1a-1), (P1a-2), (P1a-3) or (P1b),
2) a diazomethane derivative of the following general formula (P2),
3) a glyoxime derivative of the following general formula (P3),
4) a bissulfone derivative of the following general formula (P4),
5) a sulfonic acid ester of an N-hydroxyimide compound of the following general formula (P5),
6) a β-ketosulfonic acid derivative,
7) a disulfone derivative,
8) a nitrobenzylsulfonate derivative, and
9) a sulfonic acid ester derivative, but is not particularly limited thereto. Herein, these acid generating agents can be used alone, or two or more thereof can be used in combination.

[Formula 21]

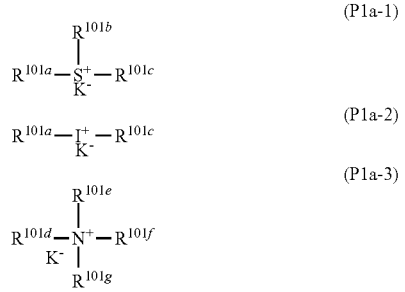

(In the above formulae, each of $R^{101a}$, $R^{101b}$ and $R^{101c}$ independently represents a linear, branched or cyclic alkyl group, alkenyl group, oxoalkyl group or oxoalkenyl group having 1 to 12 carbon atoms; an aryl group having 6 to 20 carbon atoms; or an aralkyl group or aryloxoalkyl group having 7 to 12 carbon atoms, and a part or all of hydrogen atoms of these groups may be substituted with an alkoxy group or the like. In addition, $R^{101b}$ and $R^{101c}$ may form a ring, and if forming a ring, each of $R^{101b}$ and $R^{101c}$ independently represents an alkylene group having 1 to 6 carbon atoms. $K^-$ represents a non-nucleophilic counter ion. $R^{101d}$, $R^{101e}$, $R^{101f}$ and $R^{101g}$ are represented by each independently adding a hydrogen atom to $R^{101a}$, $R^{101b}$ and $R^{101c}$. $R^{101d}$ and $R^{101e}$, and $R^{101d}$, $R^{101e}$ and $R^{101f}$ may form a ring, and if forming a ring, $R^{101d}$ and $R^{101e}$, and $R^{101d}$, $R^{101e}$ and $R^{101f}$ represent an alkylene group having 3 to 10 carbon atoms, or a heteroaromatic ring having therein the nitrogen atom(s) in the formula.)

$R^{101a}$, $R^{101b}$, $R^{101c}$, $R^{101d}$, $R^{101e}$, $R^{101f}$ and $R^{101g}$ described above may be the same or different from one another. Specifically, examples of the alkyl group include, but are not limited to the following, a methyl group, an ethyl group, a propyl group, an isopropyl group, a n-butyl group, a sec-butyl group, a tert-butyl group, a pentyl group, a hexyl group, a heptyl group, an octyl group, a cyclopentyl group, a cyclohexyl group, a cycloheptyl group, a cyclopropylmethyl group, a 4-methylcyclohexyl group, a cyclohexylmethyl group, a norbornyl group, and an adamantyl group. Examples of the alkenyl group include, but are not limited to the following, a vinyl group, an allyl group, a propenyl group, a butenyl group, a hexenyl group, and a cyclohexenyl group. Examples of the oxoalkyl group include, but are not limited to the following, a 2-oxocyclopentyl group, and a 2-oxocyclohexyl group, and can include a 2-oxopropyl group, a 2-cyclopentyl-2-oxoethyl group, a 2-cyclohexyl-2-oxoethyl group, and a 2-(4-methylcyclohexyl)-2-oxoethyl group. Examples of the oxoalkenyl group include, but are not limited to the following, a 2-oxo-4-cyclohexenyl group and a 2-oxo-4-propenyl group. Examples of the aryl group include, but are not limited to the following, a phenyl group, a naphthyl group, and alkoxyphenyl groups such as a p-methoxyphenyl group, a m-methoxyphenyl group, an o-methoxyphenyl group, an ethoxyphenyl group, a p-tert-butoxyphenyl group, and a m-tert-butoxyphenyl group; alkylphenyl groups such as a 2-methylphenyl group, a 3-methylphenyl group, a 4-methylphenyl group, an ethylphenyl group, a 4-tert-butylphenyl group, a 4-butylphenyl group, and a dimethylphenyl group; alkylnaphthyl groups such as a methylnaphthyl group and an ethylnaphthyl group; alkoxynaphthyl groups such as a methoxynaphthyl group and an ethoxynaphthyl group; dialkylnaphthyl groups such as a dimethylnaphthyl group and a diethylnaphthyl group; and dialkoxynaphthyl groups such as a dimethoxynaphthyl group and a diethoxynaphthyl group. Examples of the aralkyl group include, but are not limited to the following, a benzyl group, a phenylethyl group, and a phenethyl group. Examples of the aryloxoalkyl group include, but are not limited to the following, 2-aryl-2-oxoethyl groups such as a 2-phenyl-2-oxoethyl group, a 2-(1-naphthyl)-2-oxoethyl group, and a 2-(2-naphthyl)-2-oxoethyl group. Examples of the non-nucleophilic counter ion, $K^-$, include, but are not limited to the following, halide ions such as a chloride ion and a bromide ion; fluoroalkyl sulfonates such as triflate, 1,1,1-trifluoroethane sulfonate, and nonafluorobutane sulfonate; aryl sulfonates such as tosylate, benzene sulfonate, 4-fluorobenzene sulfonate, and 1,2,3,4,5-pentafluorobenzene sulfonate; and alkyl sulfonates such as mesylate and butane sulfonate.

In the case where $R^{101d}$, $R^{101e}$, $R^{101f}$ and $R^{101g}$ are each a heteroaromatic ring having the nitrogen atom(s) in the formula, examples of the heteroaromatic ring include imidazole derivatives (for example, imidazole, 4-methylimidazole, and 4-methyl-2-phenylimidazole), pyrazole derivatives, furazan derivatives, pyrroline derivatives (for example, pyrroline and 2-methyl-1-pyrroline), pyrrolidine derivatives (for example, pyrrolidine, N-methylpyrrolidine, pyrrolidinone, and N-methylpyrrolidone), imidazoline derivatives, imidazolidine derivatives, pyridine derivatives (for example, pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 1-methyl-2-pyridone, 4-pyrrolidinopyridine, 1-methyl-4-phenylpyridine, 2-(1-ethylpropyl)pyridine, aminopyridine, and dimethylaminopyridine), pyridazine derivatives, pyrimidine derivatives, pyrazine derivatives, pyrazoline derivatives, pyrazolidine derivatives, piperidine derivatives, piperazine derivatives, morpholine derivatives, indole derivatives, isoindole derivatives, 1H-indazole derivatives, indoline derivatives, quinoline derivatives (for example, quinoline and 3-quinolinecarbonitrile), isoquinoline derivatives, cinnoline derivatives, quinazoline derivatives, quinoxaline derivatives, phthalazine derivatives, purine derivatives, pteridin derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivative, and uridine derivatives.

The onium salts represented by the general formula (P1a-1) and the general formula (P1a-2) serve as a photo acid generating agent and a thermal acid generating agent. The onium salts of the general formula (P1a-3) serve as a thermal acid generating agent.

[Formula 22]

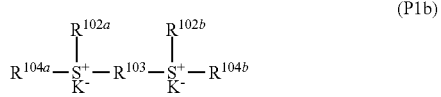

(In the formula (P1b), each of $R^{102a}$ and $R^{102b}$ independently represents a linear, branched or cyclic alkyl group having 1 to 8 carbon atoms. $R^{103}$ represents a linear, branched or cyclic alkylene group having 1 to 10 carbon atoms. Each of $R^{104a}$ and $R^{104b}$ independently represents a 2-oxoalkyl group having 3 to 7 carbon atoms. $K^-$ represents a non-nucleophilic counter ion.)

Specific examples of $R^{102a}$ and $R^{102b}$ include, but are not limited to the following, a methyl group, an ethyl group, a propyl group, an isopropyl group, a n-butyl group, a sec-butyl group, a tert-butyl group, a pentyl group, a hexyl group, a heptyl group, an octyl group, a cyclopentyl group, a cyclohexyl group, a cyclopropylmethyl group, a 4-methyl cyclohexyl group, and a cyclohexylmethyl group. Specific examples of $R^{103}$ include, but are not limited to the following, a methylene group, an ethylene group, a propylene group, a butylene group, a pentylene group, a hexylene group, a heptylene group, an octylene group, a nonylene group, a 1,4-cyclohexylene group, a 1,2-cyclohexylene group, a 1,3-cyclopentylene group, a 1,4-cyclooctylene group, and a 1,4-cyclohexanedimethylene group. Specific examples of $R^{104a}$ and $R^{104b}$ include, but are not limited to the following, a 2-oxopropyl group, a 2-oxocyclopentyl group, a 2-oxocyclohexyl group, and a 2-oxocycloheptyl group. $K^-$ includes the same as those described in the formula (P1a-1), (P1a-2) and (P1a-3).

[Formula 23]

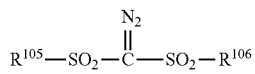

(P2)

(In the formula (P2), each of $R^{105}$ and $R^{106}$ independently represents a linear, branched or cyclic alkyl group or halogenated alkyl group having 1 to 12 carbon atoms, an aryl group or halogenated aryl group having 6 to 20 carbon atoms, or an aralkyl group having 7 to 12 carbon atoms.)

Examples of the alkyl group in each of $R^{105}$ and $R^{106}$ include, but are not limited to the following, a methyl group, an ethyl group, a propyl group, an isopropyl group, a n-butyl group, a sec-butyl group, a tert-butyl group, a pentyl group, a hexyl group, a heptyl group, an octyl group, an amyl group, a cyclopentyl group, a cyclohexyl group, a cycloheptyl group, a norbornyl group, and an adamantyl group. Examples of the halogenated alkyl group include, but are not limited to the following, a trifluoromethyl group, a 1,1,1-trifluoroethyl group, a 1,1,1-trichloroethyl group, and a nonafluorobutyl group. Examples of the aryl group include, but are not limited to the following, alkoxyphenyl groups such as a phenyl group, a p-methoxyphenyl group, a m-methoxyphenyl group, an o-methoxyphenyl group, an ethoxyphenyl group, a p-tert-butoxyphenyl group, and a m-tert-butoxyphenyl group; and alkylphenyl groups such as a 2-methylphenyl group, a 3-methylphenyl group, a 4-methylphenyl group, an ethylphenyl group, a 4-tert-butylphenyl group, a 4-butylphenyl group, and a dimethylphenyl group. Examples of the halogenated aryl group include, but are not limited to the following, a fluorophenyl group, a chlorophenyl group, and a 1,2,3,4,5-pentafluorophenyl group. Examples of the aralkyl group include, but are not limited to the following, a benzyl group and a phenethyl group.

[Formula 24]

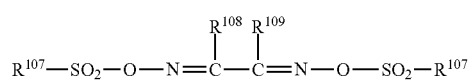

(P3)

(In the formula (P3), each of $R^{107}$, $R^{108}$ and $R^{109}$ independently represents a linear, branched or cyclic alkyl group or halogenated alkyl group having 1 to 12 carbon atoms; an aryl group or halogenated aryl group having 6 to 20 carbon atoms; or an aralkyl group having 7 to 12 carbon atoms. $R^{108}$ and $R^{109}$ may be bonded with each other to form a cyclic structure, and if forming a cyclic structure, each of $R^{108}$ and $R^{109}$ represents a linear or branched alkylene group having 1 to 6 carbon atoms.)

The alkyl group, halogenated alkyl group, aryl group, halogenated aryl group, and aralkyl group in each of $R^{107}$, $R^{108}$ and $R^{109}$ include the same as those described in $R^{105}$ and $R^{106}$. Herein, examples of the alkylene group in each of $R^{108}$ and $R^{109}$ include, but are not limited to the following, a methylene group, an ethylene group, a propylene group, a butylene group, and a hexylene group.

[Formula 25]

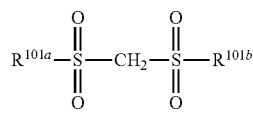

(P4)

(In the formula (P4), $R^{101a}$ and $R^{101b}$ are the same as those described above.)

[Formula 26]

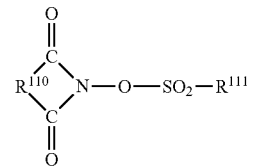

(P5)

(In the formula (P5), $R^{110}$ represents an arylene group having 6 to 10 carbon atoms, an alkylene group having 1 to 6 carbon atoms, or an alkenylene group having 2 to 6 carbon atoms. A part or all of hydrogen atoms of these groups may be further substituted with a linear or branched alkyl group or alkoxy group having 1 to 4 carbon atoms, a nitro group, an acetyl group, or a phenyl group. $R^{111}$ represents a linear, branched or substituted alkyl group, alkenyl group or alkoxyalkyl group having 1 to 8 carbon atoms, a phenyl group, or a naphthyl group. A part or all of hydrogen atoms of these groups may be further substituted with an alkyl group or alkoxy group having 1 to 4 carbon atoms; a phenyl group that may be substituted with an alkyl group or alkoxy group having 1 to 4 carbon atoms, a nitro group, or an acetyl group; a heteroaromatic group having 3 to 5 carbon atoms; or a chlorine atom or a fluorine atom.)

Herein, examples of the arylene group in $R^{110}$ include, but are not limited to the following, a 1,2-phenylene group and a 1,8-naphthylene group. Examples of the alkylene group include, but are not limited to the following, a methylene group, an ethylene group, a trimethylene group, a tetramethylene group, a phenylethylene group, and a norbornane-2,3-diyl group. Examples of the alkenylene group include, but are not limited to the following, a 1,2-vinylene group, a 1-phenyl-1,2-vinylene group, and a 5-norbornene-2,3-diyl group. The alkyl group in R" includes the same as those in $R^{101a}$ to $R^{101c}$. Examples of the alkenyl group include, but are not limited to the following, a vinyl group, a 1-propenyl group, an allyl group, a 1-butenyl group, a 3-butenyl group, an isoprenyl group, a 1-pentenyl group, a 3-pentenyl group, a 4-pentenyl group, a dimethylallyl group, a 1-hexenyl group, a 3-hexenyl group, a 5-hexenyl group, a 1-heptenyl group, a 3-heptenyl group, a 6-heptenyl group, and a 7-octenyl group. Examples of the alkoxyalkyl group include, but are not limited to the following, a methoxymethyl group, an ethoxymethyl group, a propoxymethyl group, a butoxymethyl group, a pentyloxymethyl group, a hexyloxymethyl group, a heptyloxymethyl group, a methoxyethyl group, an ethoxyethyl group, a propoxyethyl group, a butoxyethyl group, a pentyloxyethyl group, a hexyloxyethyl group, a methoxypropyl group, an ethoxypropyl group, a propoxypropyl group, a butoxypropyl group, a methoxybutyl group, an ethoxybutyl group, a propoxybutyl group, a methoxypentyl group, an ethoxypentyl group, a methoxyhexyl group, and a methoxyheptyl group.

Herein, examples of the alkyl group having 1 to 4 carbon atoms, which may be further substituted, include, but are not limited to the following, a methyl group, an ethyl group, a propyl group, an isopropyl group, a n-butyl group, a an isobutyl group, and a tert-butyl group. Examples of the alkoxy group having 1 to 4 carbon atoms include, but are not limited to the following, a methoxy group, an ethoxy group, a propoxy group, an isopropoxy group, a n-butoxy group, an isobutoxy group, and tert-butoxy group. Examples of the phenyl group that may be substituted with an alkyl group or alkoxy group having 1 to 4 carbon atoms, a nitro group, or an acetyl group include, but are not limited to the following, a phenyl group, a tolyl group, a p-tert-butoxyphenyl group, a p-acetylphenyl group, and a p-nitrophenyl group. Examples of the heteroaromatic group having 3 to 5 carbon atoms include, but are not limited to the following, a pyridyl group and a furyl group.

Specific examples of the acid generating agent include, but are not limited to the following, onium salts such as tetramethylammonium trifluoromethanesulfonate, tetramethylammonium nonafluorobutanesulfonate, triethylammonium nonafluorobutanesulfonate, pyridinium nonafluorobutanesulfonate, triethylammonium camphorsulfonate, pyridinium camphorsulfonate, tetra n-butylammonium nonafluorobutanesulfonate, tetraphenylammonium nonafluorobutanesulfonate, tetramethylammonium p-toluenesulfonate, diphenyliodonium trifluoromethanesulfonate, (p-tert-butoxyphenyl)phenyliodonium trifluoromethanesulfonate, diphenyliodonium p-toluenesulfonate, (p-tert-butoxyphenyl)phenyliodonium p-toluenesulfonate, triphenylsulfonium trifluoromethanesulfonate, (p-tert-butoxyphenyl)diphenylsulfonium trifluoromethanesulfonate, bis(p-tert-butoxyphenyl)phenylsulfonium trifluoromethanesulfonate, tris(p-tert-butoxyphenyl)sulfonium trifluoromethanesulfonate, triphenylsulfonium p-toluenesulfonate, (p-tert-butoxyphenyl)diphenylsulfonium p-toluenesulfonate, bis(p-tert-butoxyphenyl)phenylsulfonium p-toluenesulfonate, tris(p-tert-butoxyphenyl)sulfonium p-toluenesulfonate, triphenylsulfonium nonafluorobutanesulfonate, triphenylsulfonium butanesulfonate, trimethylsulfonium trifluoromethanesulfonate, trimethylsulfonium p-toluenesulfonate, cyclohexylmethyl(2-oxocyclohexyl)sulfonium trifluoromethanesulfonate, cyclohexylmethyl(2-oxocyclohexyl)sulfonium p-toluenesulfonate, dimethylphenylsulfonium trifluoromethanesulfonate, dimethylphenylsulfonium p-toluenesulfonate, dicyclohexylphenylsulfonium trifluoromethanesulfonate, dicyclohexylphenylsulfonium p-toluenesulfonate, trinaphthylsulfonium trifluoromethanesulfonate, cyclohexylmethyl(2-oxocyclohexyl)sulfonium trifluoromethanesulfonate, (2-norbornyl)methyl(2-oxocyclohexyl)sulfonium trifluoromethanesulfonate, ethylene bis[methyl(2-oxocyclopentyl)sulfonium trifluoromethanesulfonate], and 1,2'-naphthylcarbonylmethyltetrahydrothiophenium triflate; diazomethane derivatives such as bis(benzenesulfonyl)diazomethane, bis(p-toluenesulfonyl)diazomethane, bis(xylenesulfonyl)diazomethane, bis(cyclohexylsulfonyl)diazomethane, bis(cyclopentylsulfonyl)diazomethane, bis(n-butylsulfonyl)diazomethane, bis(isobutylsulfonyl)diazomethane, bis(sec-butylsulfonyl)diazomethane, bis(n-propylsulfonyl)diazomethane, bis(isopropylsulfonyl)diazomethane, bis(tert-butylsulfonyl)diazomethane, bis(n-amylsulfonyl)diazomethane, bis(isoamylsulfonyl)diazomethane, bis(sec-amylsulfonyl)diazomethane, bis(tert-amylsulfonyl)diazomethane, 1-cyclohexylsulfonyl-1-(tert-butylsulfonyl)diazomethane, 1-cyclohexylsulfonyl-1-(tert-amylsulfonyl)diazomethane, and 1-tert-amylsulfonyl-1-(tert-butylsulfonyl)diazomethane; glyoxime derivatives such as bis-(p-toluenesulfonyl)-α-dimethylglyoxime, bis-(p-toluesulfonyl)-α-diphenylglyoxime, bis-(p-toluenesulfonyl)-α-dicyclohexylglyoxime, bis-(p-toluenesulfonyl)-2,3-pentanedioneglyoxime, bis-(p-toluenesulfonyl)-2-methyl-3,4-pentanedioneglyoxime, bis-(n-butanesulfonyl)-α-dimethylglyoxime, bis-(n-butanesulfonyl)-α-diphenylglyoxime, bis-(n-butanesulfonyl)-α-dicyclohexylglyoxime, bis-(n-butanesulfonyl)-2,3-pentanedioneglyoxime, bis-(n-butanesulfonyl)-2-methyl-3,4-pentanedioneglyoxime, bis-(methanesulfonyl)-α-dimethylglyoxime, bis-(trifluoromethanesulfonyl)-α-dimethylglyoxime, bis-(1,1,1-trifluoroethanesulfonyl)-α-dimethylglyoxime, bis-(tert-butanesulfonyl)-α-dimethylglyoxime, bis-(perfluorooctanesulfonyl)-α-dimethylglyoxime, bis-(cyclohexanesulfonyl)-α-dimethylglyoxime, bis-(benzenesulfonyl)-α-dimethylglyoxime, bis-(p-fluorobenzenesulfonyl)-α-dimethylglyoxime, bis-(p-tert-butylbenzenesulfonyl)-α-dimethylglyoxime, bis-(xylenesulfonyl)-α-dimethylglyoxime, and bis-(camphorsulfonyl)-α-dimethylglyoxime; bissulfone derivatives, such as bisnaphthylsulfonylmethane, bistrifluoromethylsulfonylmethane, bismethylsulfonylmethane, bisethylsulfonylmethane, bispropylsulfonylmethane, bisisopropylsulfonylmethane, bis-p-toluenesulfonylmethane, and bisbenzenesulfonylmethane; β-ketosulfone derivatives such as 2-cyclohexylcarbonyl-2-(p-toluenesulfonyl)propane and 2-isopropylcarbonyl-2-(p-toluenesulfonyl)propane; disulfone derivatives such as a diphenyldisulfone derivative and a dicyclohexyldisulfone derivative; nitrobenzylsulfonate derivatives such as 2,6-dinitrobenzyl p-toluenesulfonate and 2,4-dinitrobenzyl p-toluenesulfonate; sulfonic acid ester derivatives such as 1,2,3-tris(methanesulfonyloxy)benzene, 1,2,3-tris(trifluoromethanesulfonyloxy)benzene, and 1,2,3-tris(p-toluenesulfonyloxy)benzene; and sulfonic acid ester derivatives of a N-hydroxyimide compound, such as N-hydroxysuccinimide methanesulfonic acid ester, N-hydroxysuccinimide trifluoromethanesulfonic acid ester, N-hydroxysuccinimide ethanesulfonic acid ester, N-hydroxysuccinimide 1-propanesulfonic acid ester, N-hydroxysuccinimide 2-propanesulfonic acid ester, N-hydroxysuccinimide 1-pentanesulfonic acid ester, N-hydroxysuccinimide 1-octanesulfonic acid ester, N-hydroxysuccinimide p-toluenesulfonic acid ester, N-hydroxysuccinimide p-methoxybenzenesulfonic acid ester, N-hydroxysuccinimide 2-chloroethanesulfonic acid ester, N-hydroxysuccinimide benzenesulfonic acid ester, N-hydroxysuccinimide-2,4,6-trimethylbenzenesulfonic acid ester, N-hydroxysuccinimide 1-naphthalenesulfonic acid ester, N-hydroxysuccinimide 2-naphthalenesulfonic acid ester, N-hydroxy-2-phenylsuccinimide methanesulfonic acid ester, N-hydroxymaleimide methanesulfonic acid ester, N-hydroxymaleimide ethanesulfonic acid ester, N-hydroxy-2-phenylmaleimide methanesulfonic acid ester, N-hydroxyglutarimide methanesulfonic acid ester, N-hydroxyglutarimide benzenesulfonic acid ester, N-hydroxyphthalimide methanesulfonic acid ester, N-hydroxyphthalimide benzenesulfonic acid ester, N-hydroxyphthalimide trifluoromethanesulfonic acid ester, N-hydroxyphthalimide p-toluenesulfonic acid ester, N-hydroxynaphthalimide methanesulfonic acid ester, N-hydroxynaphthalimide benzenesulfonic acid ester, N-hydroxy-5-norbornene-2,3-dicarboxyimide methanesulfonic acid ester, N-hydroxy-5-norbornene-2,3-dicarboxyimide trifluoromethanesulfonic acid ester, and N-hydroxy-5-norbornene-2,3-dicarboxyimide p-toluenesulfonic acid ester.

Among them, in particular, onium salts such as triphenylsulfonium trifluoromethanesulfonate, (p-tert-butoxyphenyl)diphenylsulfonium trifluoromethanesulfonate, tris(p-tert-butoxyphenyl)sulfonium trifluoromethanesulfonate, triphenylsulfonium p-toluenesulfonate, (p-tert-butoxyphenyl)diphenylsulfonium p-toluenesulfonate, tris(p-tert-butoxyphenyl)sulfonium p-toluenesulfonate, trinaphthylsulfonium trifluoromethanesulfonate, cyclohexylmethyl(2-oxocyclohexyl)sulfonium trifluoromethanesulfonate, (2-norbornyl)methyl(2-oxocyclohexyl)sulfonium trifluoromethanesulfonate, and 1,2'-naphthylcarbonylmethyltetrahydrothiophenium triflate; diazomethane derivatives such as bis(benzenesulfonyl)diazomethane, bis(p-toluenesulfonyl)diazomethane, bis(cyclohexylsulfonyl)diazomethane, bis(n-butylsulfonyl)diazomethane, bis(isobutylsulfonyl)diazomethane, bis(sec-butylsulfonyl)diazomethane, bis(n-propylsulfonyl)diazomethane, bis(isopropylsulfonyl)diazomethane, and bis(tert-butylsulfonyl)diazomethane; glyoxime derivatives such as bis-(p-toluenesulfonyl)-α-dimethylglyoxime and bis-(n-butanesulfonyl)-α-dimethylglyoxime, bissulfone derivatives such as bisnaphthylsulfonylmethane; and sulfonic acid ester derivatives of an N-hydroxyimide compound, such as N-hydroxysuccinimide methanesulfonic acid ester, N-hydroxysuccinimide trifluoromethanesulfonic acid ester, N-hydroxysuccinimide 1-propanesulfonic acid ester, N-hydroxysuccinimide 2-propanesulfonic acid ester, N-hydroxysuccinimide 1-pentanesulfonic acid ester, N-hydroxysuccinimide p-toluenesulfonic acid ester, N-hydroxynaphthalimide methanesulfonic acid ester, and N-hydroxynaphthalimide benzenesulfonic acid ester are preferably used.

In the material for forming an underlayer film for lithography according to the present embodiment, the content of the acid generating agent is not particularly limited, but the content is preferably 0.1 to 50 parts by mass and more preferably 0.5 to 40 parts by mass, based on 100 parts by mass of the compound represented by the general formula (1) and/or the resin having a structure represented by the general formula (2). The content is set within the above range to result in a tendency to increase the acid generation amount to promote a crosslinking reaction, and also to result in a tendency to suppress the occurrence of the mixing phenomenon with a resist layer.

Furthermore, the material for forming an underlayer film for lithography of the present embodiment may contain a basic compound from the viewpoint of improving preservation stability.

The basic compound serves as a quencher to an acid for preventing a trace amount of the acid generated from the acid generating agent from promoting a crosslinking reaction. Examples of such a basic compound include primary, secondary, and tertiary aliphatic amines, mixed amines, aromatic amines, heterocyclic amines, a nitrogen-containing compound having a carboxy group, a nitrogen-containing compound having a sulfonyl group, a nitrogen-containing compound having a hydroxyl group, a nitrogen-containing compound having a hydroxyphenyl group, an alcoholic nitrogen-containing compound, an amide derivative, and an imide derivative, but are not particularly limited thereto.

Specifically, specific examples of the primary aliphatic amines include, but are not limited to the following, ammonia, methylamine, ethylamine, n-propylamine, isopropylamine, n-butylamine, isobutylamine, sec-butylamine, tert-butylamine, pentylamine, tert-amylamine, cyclopentylamine, hexylamine, cyclohexylamine, heptylamine, octylamine, nonylamine, decylamine, dodecylamine, cetylamine, methylenediamine, ethylenediamine, and tetraethylenepentamine. Specific examples of the secondary aliphatic amines include, but are not limited to the following, dimethylamine, diethylamine, di-n-propylamine, diisopropylamine, di-n-butylamine, diisobutylamine, di-sec-butylamine, dipentylamine, dicyclopentylamine, dihexylamine, dicyclohexylamine, diheptylamine, dioctylamine, dinonylamine, didecylamine, didodecylamine, dicetylamine, N,N-dimethylmethylenediamine, N,N-dimethylethylenediamine, and N,N-dimethyltetraethylenepentamine. Specific examples of the tertiary aliphatic amines include, but are not limited to the following, trimethylamine, triethylamine, tri-n-propylamine, triisopropylamine, tri-n-butylamine, triisobutylamine, tri-sec-butylamine, tripentylamine, tricyclopentylamine, trihexylamine, tricyclohexylamine, triheptylamine, trioctylamine, trinonylamine, tridecylamine, tridodecylamine, tricetylamine, N,N,N',N'-tetramethylmethylenediamine, N,N,N',N'-tetramethylethylenediamine, and N,N,N',N'-tetramethyltetraethylenepentamine.

Specific examples of the mixed amines include, but are not limited to the following, dimethylethylamine, methylethylpropylamine, benzylamine, phenethylamine, and benzyldimethylamine. Specific examples of the aromatic amines and heterocyclic amines include, but are not limited to the following, aniline derivatives (for example, aniline, N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline, and N,N-dimethyltoluidine), diphenyl(p-tolyl)amine, methyldiphenylamine, triphenylamine, phenylenediamine, naphthylamine, diaminonaphthalene, pyrrole derivatives (for example, pyrrole, 2H-pyrrole, 1-methylpyrrole, 2,4-dimethylpyrrole, 2,5-dimethylpyrrole, and N-methylpyrrole), oxazole derivatives (for example, oxazole and isoxazole), thiazole derivatives (for example, thiazole and isothiazole), imidazole derivatives (for example, imidazole, 4-methylimidazole, and 4-methyl-2-phenylimidazole), pyrazole derivatives, furazan derivatives, pyrroline derivatives (for example, pyrroline and 2-methyl-1-pyrroline), pyrrolidine derivatives (for example, pyrrolidine, N-methylpyrrolidine, pyrrolidinone, and N-methylpyrrolidone), imidazoline derivatives, imidazolidine derivatives, pyridine derivatives (for example, pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 1-methyl-2-pyridone, 4-pyrrolidinopyridine, 1-methyl-4-phenylpyridine, 2-(1-ethylpropyl)pyridine, aminopyridine, and dimethylaminopyridine), pyridazine derivatives, pyrimidine derivatives, pyrazine derivatives, pyrazoline derivatives, pyrazolidine derivatives, piperidine derivatives, piperazine derivatives, morpholine derivatives, indole derivatives, isoindole derivatives, 1H-indazole derivatives, indoline derivatives, quinoline derivatives (for example, quinoline, 3-quinolinecarbonitrile), isoquinoline derivatives, cinnoline derivatives, quinazoline derivatives, quinoxaline derivatives, phthalazine derivatives, purine derivatives, pteridin derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivatives, and uridine derivatives.

Furthermore, specific examples of the nitrogen-containing compound having a carboxy group include, but are not limited to the following, aminobenzoic acid, indolecarboxylic acid, and amino acid derivatives (for example, nicotinic acid, alanine, arginine, aspartic acid, glutamic acid, glycine, histidine, isoleucine, glycylleucine, leucine, methionine, phenylalanine, threonine, lysine, 3-aminopyrazine-2-carboxylic acid, and methoxyalanine). Specific examples of the nitrogen-containing compound having a sulfonyl group include, but are not limited to the following, 3-pyridinesulfonic acid and pyridinium p-toluenesulfonate. Specific examples of the nitrogen-containing compound having a hydroxyl group, the nitrogen-containing compound having a hydroxyphenyl group, and the alcoholic nitrogen-containing compound include, but are not limited to the following, 2-hydroxypyridine, aminocresol, 2,4-quinolinediol, 3-indolemethanol hydrate, monoethanolamine, diethanolamine, triethanolamine, N-ethyldiethanolamine, N,N-diethylethanolamine, triisopropanolamine, 2,2'-iminodiethanol, 2-aminoethanol, 3-amino-1-propanol, 4-amino-1-butanol, 4-(2-hydroxyethyl)morpholine, 2-(2-hydroxyethyl)pyridine, 1-(2-hydroxyethyl)piperazine, 1-[2-(2-hydroxyethoxyl)ethyl]piperazine, piperidine ethanol, 1-(2-hydroxyethyl)pyrrolidine, 1-(2-hydroxyethyl)-2-pyrrolidone, 3-piperidino-1,2-propanediol, 3-pyrrolidino-1,2-propanediol, 8-hydroxyjulolidine, 3-quinuclidinol, 3-tropanol, 1-methyl-2-pyrrolidine ethanol, 1-aziridine ethanol, N-(2-hydroxyethyl)phthalimide, and N-(2-hydroxyethyl)isonicotinamide. Specific examples of the amide derivative include, but are not limited to the following, formamide, N-methylformamide, N,N-dimethylformamide, acetamide, N-methylacetamide, N,N-dimethylacetamide, propionamide, and benzamide. Specific examples of the imide derivative include, but are not limited to the following, phthalimide, succinimide, and maleimide.

In the material for forming an underlayer film for lithography according to the present embodiment, the content of the basic compound is not particularly limited, but the content is preferably 0.001 to 2 parts by mass and more preferably 0.01 to 1 parts by mass, based on 100 parts by mass of the compound represented by the general formula (1) and the resin having a structure represented by the general formula (2). The content is set within the above preferable range to result in a tendency to improve preservation stability without excessively interrupting a crosslinking reaction.

In addition, the material for forming an underlayer film for lithography of the present embodiment may contain other resins and/or compounds for the purpose of imparting heat curability and controlling absorbance. Such other resins and/or compounds include naphthol resins, xylene resins, naphthol-modified resins, phenol-modified resins of naphthalene resins, polyhydroxystyrene, dicyclopentadiene resins, (meth)acrylate, dimethacrylate, trimethacrylate, tetramethacrylate, resins having a naphthalene ring such as vinylnaphthalene and polyacenaphthylene, resins having a biphenyl ring such as phenanthrenequinone and fluorene, resins having a heterocyclic ring having a hetero atom such as thiophene and indene, and resins not containing an aromatic ring; rosin-based resins, and resins or compounds including an alicyclic structure, such as cyclodextrin, adamantane(poly)ol, tricyclodecane(poly)ol and derivatives thereof, but are not particularly limited thereto. Furthermore, the material for forming an underlayer film for lithography of the present embodiment may also contain known additives. Examples of the known additives include, but are not limited to the following, an ultraviolet absorber, a surfactant, a colorant, and a non-ionic surfactant.

The material for forming an underlayer film for lithography according to the present embodiment may contain an organic solvent. As the organic solvent, a known one can be appropriately used as long as it dissolves at least the compound represented by general formula (1) and/or the resin having a structure represented by the general formula (2).

Specific examples of the organic solvent include ketone-based solvents such as acetone, methyl ethyl ketone, methyl isobutyl ketone, and cyclohexanone; cellosolve-based solvents such as propylene glycol monomethyl ether and propylene glycol monomethyl ether acetate; ester-based solvents such as ethyl lactate, methyl acetate, ethyl acetate, butyl acetate, isoamyl acetate, ethyl lactate, methyl methoxypropionate, and methyl hydroxyisobutyrate; alcohol-based solvents such as methanol, ethanol, isopropanol, and 1-ethoxy-2-propanol; and aromatic hydrocarbons such as toluene, xylene, and anisole, but are not particularly limited thereto. These organic solvents can be used alone, or two or more thereof can be used in combination.

Among the above organic solvents, particularly preferable are cyclohexanone, propylene glycol monomethyl ether, propylene glycol monomethyl ether acetate, ethyl lactate, methyl hydroxyisobutyrate, anisole, in terms of safety.

The content of the organic solvent is not particularly limited, but it is preferably 100 to 10,000 parts by mass and more preferably 200 to 5,000 parts by mass, based on 100 parts by mass of the compound represented by the general formula (1) and/or the resin having a structure represented by the general formula (2), from the viewpoint of solubility and film formability.

[Underlayer Film for Lithography and Forming Method of Multilayer Resist Pattern]

An underlayer film for lithography of the present embodiment is formed from the material for forming an underlayer film for lithography of the present embodiment.

In addition, a pattern forming method of the present embodiment includes step (A-1) of forming an underlayer film on a substrate by using the material for forming an underlayer film for lithography of the present embodiment, step (A-2) of forming at least one photoresist layer on the underlayer film, and step (A-3) of irradiating a predetermined region of the photoresist layer with radiation and developing it with an alkali, after the second formation step.

Furthermore, another pattern forming method of the present embodiment includes step (B-1) of forming an underlayer film on a substrate by using the material for forming an underlayer film for lithography of the present embodiment, step (B-2) of forming an intermediate layer film on the underlayer film by using a silicon atom-containing resist intermediate layer film material, step (B-3) of forming at least one photoresist layer on the intermediate layer film, step (B-4) of irradiating a predetermined region of the photoresist layer with radiation and developing it with an alkali to form a resist pattern, after step (B-3), and step (B-5) of etching the intermediate layer film while the resist pattern functions as a mask, etching the underlayer film while the obtained intermediate layer film pattern functions as an etching mask and etching the substrate while the obtained underlayer film pattern functions as an etching mask to form a pattern on the substrate, after step (B-4).

The underlayer film for lithography of the present embodiment is not particularly limited in terms of the forming method thereof as long as it is formed from the material for forming an underlayer film for lithography of the present embodiment, and a method known can be applied. For example, the underlayer film can be formed by applying the material for forming an underlayer film for lithography of the present embodiment on the substrate by a known coating method or printing method such as spin coating or screen printing, and removing an organic solvent by volatilization or the like. The underlayer film is preferably baked upon forming in order to suppress the occurrence of the mixing phenomenon with an upperlayer resist and also promote a crosslinking reaction. In this case, the baking temperature is not particularly limited, but it is preferably within the range of 80 to 450° C., and more preferably 200 to 400° C. In addition, the baking time is not also particularly limited, but is preferably within the range of 10 to 300 seconds. Herein, the thickness of the underlayer film can be appropriately selected depending on the required properties, and is not particularly limited, but the thickness is usually preferably about 30 to 20,000 nm and more preferably 50 to 15,000 nm. After the underlayer film is prepared, in the case of a two-layer process, a silicon-containing resist layer or a usual single-layer resist including a hydrocarbon is prepared on the underlayer film, and in the case of a three-layer process, a silicon-containing intermediate layer is prepared on the underlayer film, and a single-layer resist layer not containing silicon is preferably prepared on the silicon-containing intermediate layer. In these cases, a photoresist material for forming the resist layer, which can be used, is a known one.

After the underlayer film is prepared on the substrate, in the case of a two-layer process, a silicon-containing resist layer or a usual single-layer resist including a hydrocarbon can be prepared on the underlayer film, and in the case of a three-layer process, a silicon-containing intermediate layer can be prepared on the underlayer film, and a single-layer resist layer not containing silicon can be prepared on the silicon-containing intermediate layer. In these cases, a photoresist material for forming the resist layer, which can be used, is appropriately selected from known ones, and is not particularly limited.

As the silicon-containing resist material for a two-layer process, a positive-type photoresist material is preferably used, which contains a silicon atom-containing polymer such as a polysilsesquioxane derivative or a vinylsilane derivative used as a base polymer from the viewpoint of oxygen gas-etching resistance, and an organic solvent, an acid generating agent and if necessary a basic compound. Herein, as the silicon atom-containing polymer, a known polymer used in such a resist material can be used.

As the silicon-containing intermediate layer for a three-layer process, a polysilsesquioxane-based intermediate layer is preferably used. The intermediate layer tends to be allowed to have an effect as an antireflective film, thereby making it possible to effectively suppress reflection. For example, if a material including many aromatic groups and having a high substrate-etching resistance is used for the underlayer film in a 193 nm exposure process, a k-value tends to be increased to increase substrate reflection, but the reflection can be suppressed by the intermediate layer to thereby make the substrate reflection 0.5% or less. For the intermediate layer having such an antireflection effect, but are not limited to the following, polysilsesquioxane into which a phenyl group or a light-absorbing group having a silicon-silicon bond for 193 nm exposure is introduced and which is to be crosslinked with an acid or heat is preferably used.

An intermediate layer formed by the Chemical Vapour Deposition (CVD) method can also be used. As the intermediate layer having a high effect as an antireflective film, prepared by the CVD method, but are not limited to the following, for example, a SiON film is known. In general, the intermediate layer is formed by a wet process such as a spin coating method or screen printing rather than the CVD method in terms of simplicity and cost effectiveness. Herein, the upperlayer resist in a three-layer process may be of positive-type or negative-type, and the same one as a commonly used single-layer resist can be used therefor.

Furthermore, the underlayer film of the present embodiment can also be used as a usual antireflective film for use in a single-layer resist or a usual underlying material for suppressing pattern collapse. The underlayer film of the present embodiment can also be expected to serve as a hard mask for underlying processing because of being excellent in etching resistance for underlying processing.

In the case where a resist layer is formed by the photoresist material, a wet process such as a spin coating method or screen printing is preferably used as in the case of forming the underlayer film. The resist material is coated by a spin coating method or the like and then usually pre-baked, and such pre-baking is preferably performed in the range of 80 to 180° C. for 10 to 300 seconds. Thereafter, in accordance with an ordinary method, the resultant can be subjected to exposure, post-exposure bake (PEB), and development to obtain a resist pattern. Herein, the thickness of the resist film is not particularly limited, but generally, it is preferably 30 to 500 nm and more preferably 50 to 400 nm.

Light for use in exposure may be appropriately selected depending on the photoresist material to be used. In general, examples thereof include high energy radiation having a wavelength of 300 nm or less, specifically, excimer lasers of 248 nm, 193 nm, and 157 nm, a soft X-ray of 3 to 20 nm, electron beam, and an X-ray.

The resist pattern formed by the above method is a pattern whose collapse is suppressed by the underlayer film of the present embodiment. Therefore, the underlayer film of the present embodiment can be used to thereby obtain a finer pattern, and an exposure amount necessary for obtaining such a resist pattern can be reduced.

Then, the obtained resist pattern is used as a mask to perform etching. As the etching of the underlayer film in a two-layer process, gas etching is preferably used. As the gas etching, etching using oxygen gas is suitable. In addition to oxygen gas, an inert gas such as He and Ar, and CO, $CO_2$, $NH_3$, $SO_2$, $N_2$, $NO_2$, and $H_2$ gases can also be added. The gas etching can also be performed not using oxygen gas but using only CO, $CO_2$, $NH_3$, $N_2$, $NO_2$, and $H_2$ gases. In particular, the latter gases are preferably used for protecting a side wall for preventing a pattern side wall from being undercut. On the other hand, also in the etching of the intermediate layer in a three-layer process, gas etching is preferably used. As the gas etching, the same one as the one described in a two-layer process can be applied. In particular, the intermediate layer is preferably processed in a three-layer process using a fluorocarbon gas while the resist pattern functions as a mask. Thereafter, as described above, the intermediate layer pattern is used as a mask to perform, for example, oxygen gas etching, thereby processing the underlayer film.

Herein, in the case where an inorganic hard mask intermediate layer film is formed as the intermediate layer, a silicon oxide film, a silicon nitride film, and a silicon oxynitride film (SiON film) are formed by the CVD method, the ALD method, and the like. As the method for forming a nitride film, but are not limited to the following, the method described in, for example, Japanese Patent Laid-Open No. 2002-334869 and W02004/066377 can be used.

While the photoresist film can be directly formed on such an intermediate layer film, an organic antireflective film (BARC) may also be formed on the intermediate layer film by spin coating, and the photoresist film may also be formed thereon.

As the intermediate layer, a polysilsesquioxane-based intermediate layer is also preferably used. The resist intermediate layer film tends to be allowed to have an effect as an antireflective film, thereby making it possible to effectively suppress reflection. As a specific material for the polysilsesquioxane-based intermediate layer, but are not limited to the following, the material described in, for example, Japanese Patent Laid-Open No. 2007-226170 and Japanese Patent Laid-Open No. 2007-226204 can be used.

The next etching of the substrate can also be performed by an ordinary method, and, for example, when the substrate is made of $SiO_2$ or SiN, etching with mainly a fluorocarbon gas can be performed, and when the substrate is made of p-Si, Al, or W, etching mainly using a chlorine-based gas or bromine-based gas can be performed. In the case where the substrate is processed by the etching with a fluorocarbon gas, the silicon-containing resist in a two-layer resist process and the silicon-containing intermediate layer in a three-layer process are peeled off at the same time as the processing of the substrate. On the other hand, in the case where the substrate is processed by the etching with a chlorine-based gas or bromine-based gas, the silicon-containing resist layer or the silicon-containing intermediate layer is peeled off separately, and is generally peeled off by dry etching with a fluorocarbon gas after the substrate is processed.

The underlayer film of the present embodiment is characterized by being excellent in etching resistance of such a substrate.

Herein, the substrate that can be used is appropriately selected from ones known, and is not particularly limited, but includes Si, α-Si, p-Si, $SiO_2$, SiN, SiON, W, TiN, and Al substrates. In addition, the substrate may also be a laminate having a processed film (processed substrate) on a base material (support). Such a processed film includes various Low-k films made of Si, $SiO_2$, SiON, SiN, p-Si, α-Si, W, W—Si, Al, Cu, and Al—Si, and stopper films thereof, and a material different from the base material (support) is usually used therefor. Herein, the thickness of the substrate to be processed or the processed film is not particularly limited, but it is usually preferably about 50 to 10,000 nm and more preferably 75 to 5,000 nm.

EXAMPLES

Hereinafter, the present invention will be described by Synthesis Examples and Examples in more detail, but the present invention is not limited thereto at all.

(Carbon Concentration and Oxygen Concentration)

The carbon concentration and the oxygen concentration (% by mass) were measured by organic element analysis.

Apparatus: CHN CORDER MT-6 (manufactured by Yanaco Bunseki Kogyo Co.)

(Molecular Weight)

Measurement was performed by GC-MS analysis using Agilent 5975/6890N manufactured by Agilent. Alternatively, measurement was performed by LC-MS analysis using Acquity UPLC/MALDI-Synapt HDMS manufactured by Water.

(Molecular Weight in Terms of Polystyrene)

Gel permeation chromatography (GPC) analysis was used to determine the weight average molecular weight (Mw) and the number average molecular weight (Mn) in terms of polystyrene, and to determine the degree of dispersion (Mw/Mn).

Apparatus: Shodex GPC-101 type (manufactured by Showa Denko K. K.)

Column: KF-80M×3

Eluent: THF 1 ml/min

Temperature: 40° C.

(Pyrolysis Temperature (Tg))

An EXSTAR 6000 DSC apparatus manufactured by SII NanoTechnology Inc. was used, and about 5 mg of a sample was placed in an unsealed aluminum container and heated to 500° C. at a rate of temperature rise of 10° C./min in a nitrogen gas (30 ml/min) stream. In this time, a temperature at which a reducing portion appeared on the base line was defined as a pyrolysis temperature (Tg).

(Solubility)

The amount of each compound dissolved in 1-methoxy-2-propanol (PGME) and propylene glycol monomethyl ether acetate (PGMEA) was measured at 23° C., and the results were evaluated according to the following criteria.

Evaluation A: 10% by weight or more

Evaluation B: 3% by weight or more and less than 10% by weight

Evaluation C: less than 3% by weight (Synthesis Example 1) Synthesis of BisP-1

A container having an inner volume of 100 ml, equipped with a stirrer, a condenser and a burette, was prepared. To the container were charged 1.10 g (10 mmol) of hydroquinone (reagent produced by Sigma-Aldrich Co., LLC.), 1.82 g (10 mmol) of 4-biphenylaldehyde (produced by Mitsubishi Gas Chemical Company, Inc.) and 30 ml of methyl isobutyl ketone, and 5 ml of 95% sulfuric acid was added thereto to prepare a reaction liquid. The reaction liquid was stirred at 100° C. for 6 hours to perform a reaction. Then, the reaction liquid was concentrated, 50 g of pure water was added thereto to precipitate a reaction product, and the resultant was cooled to room temperature followed by filtration for separation. A solid obtained by filtration was dried, and separated and purified by column chromatography to thereby provide 1.05 g of an objective compound (BisP-1) represented by the following formula.

Herein, the following peaks were observed by 400 MHz-$^1$H-NMR, and it was confirmed that the compound had a chemical structure of the following formula.

$^1$H-NMR: (d-DMSO, Internal reference TMS)

δ (ppm) 9.6 (2H, O—H), 7.2-8.3 (15H, Ph-H), 6.6 (1H, C—H)

[Formula 27]

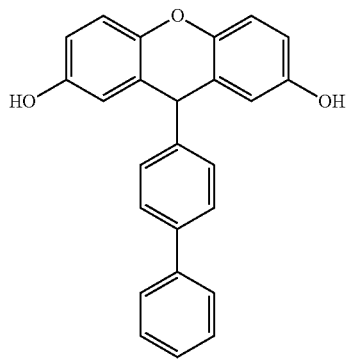

(BisP-1)

As a result of organic element analysis, the carbon concentration and the oxygen concentration of the resulting compound (BisP-1) were 82.0% and 13.0%, respectively. The carbon content rate was high and the oxygen content rate was low, and compound (BisP-1) was thus evaluated as having a high etching resistance.

The molecular weight of the resulting compound was measured by the above method, and as a result, it was 366.

As a result of thermogravimetric measurement (TG), the pyrolysis temperature of the resulting compound (BisP-1) was 350° C. or more. Therefore, the compound was evaluated as having a high heat resistance and also applicability to high-temperature baking.

The solubility in PGME and PGMEA was evaluated, and as a result, was 20% by weight or more (Evaluation A) and compound (BisP-1) was evaluated as having an excellent solubility. Therefore, compound (BisP-1) was evaluated as having a high preservation stability in a solution state and also a sufficient applicability to an edge bead rinse liquid (mixed liquid of PGME/PGMEA) widely used in a semiconductor microfabrication process.

Production Example 1

A four-neck flask having a bottom outlet and an inner volume of 10 L, equipped with a Dimroth condenser, a thermometer and a stirring blade, was prepared. To this four-neck flask were charged 1.09 kg of 1,5-dimethylnaphthalene (7 mol, produced by Mitsubishi Gas Chemical Company, Inc.), 2.1 kg of a 40% by mass aqueous formalin solution (28 mol as formaldehyde, produced by Mitsubishi Gas Chemical Company, Inc.) and 0.97 ml of 98% by mass sulfuric acid (produced by Kanto Chemical Co., Inc.) under a nitrogen stream, and allowed the reaction to run under ordinary pressure with refluxing at 100° C. for 7 hours. Thereafter, ethylbenzene (special grade chemical, produced by Wako Pure Chemical Industries, Ltd.) (1.8 kg) as a dilution solvent was added to the reaction solution and left to stand, and then an aqueous phase being a bottom phase was removed. Furthermore, the resultant was neutralized and washed with water, and ethylbenzene and the unreacted 1,5-dimethylnaphthalene were distilled off under reduced pressure, thereby providing 1.25 kg of a dimethylnaphthalene formaldehyde resin as a light-brown solid.

With respect to the molecular weight of the resulting dimethylnaphthalene formaldehyde, Mn was 562, Mw was 1168 and Mw/Mn was 2.08. In addition, the carbon concentration was 84.2% by mass, and the oxygen concentration was 8.3% by mass.

Subsequently, a four-neck flask having an inner volume of 0.5 L, equipped with a Dimroth condenser, a thermometer and a stirring blade is prepared. To this four-neck flask were charged 100 g (0.51 mol) of the dimethylnaphthalene formaldehyde resin obtained as described above and 0.05 g of paratoluenesulfonic acid under a nitrogen stream, heated for 2 hours with the temperature being raised to 190° C., and then stirred. Thereafter, 52.0 g (0.36 mol) of 1-naphthol was further added thereto, and further heated to 220° C. to allow the reaction to run for 2 hours. After being diluted with a solvent, the resultant was neutralized and washed with water, and the solvent was removed under reduced pressure to thereby provide 126.1 g of a modified resin (CR-1) as a blackish brown solid.

With respect to the resulting resin (CR-1), Mn was 885, Mw was 2220 and Mw/Mn was 4.17. In addition, the carbon concentration was 89.1% by mass and the oxygen concentration was 4.5% by mass.

Example 1, Comparative Example 1

A material for forming an underlayer film for lithography in each of Example 1 and Comparative Example 1 was prepared so as to have composition shown in Table 1. That is, the following materials were used.

Acid generating agent: di-tert-butyldiphenyliodonium nonafluoromethanesulfonate (DTDPI) produced by Midori Kagaku Co., Ltd.

Crosslinking agent: Nikalac MX270 (Nikalac) produced by Sanwa Chemical Co., Ltd.

Organic solvent: cyclohexanone (CHN)

Novolac: PSM4357 produced by Gunei Chemical Industry Co., Ltd.

Then, such a material for forming an underlayer film in each of Example 1 and Comparative Example 1 was spin-coated on a silicon substrate, thereafter baked at 240° C. for 60 seconds and further at 400° C. for 120 seconds to prepare each underlayer film having a film thickness of 200 nm.

An etching test was performed under conditions shown below to evaluate etching resistance. The evaluation results are shown in Table 1.

[Etching Test]

Etching apparatus: RIE-10NR manufactured by Samco Inc.

Output: 50 W

Pressure: 20 Pa

Time: 2 min

Etching Gas

Ar gas flow rate:$CF_4$ gas flow rate:$O_2$ gas flow rate=50:5:5 (sccm)

[Evaluation of Etching Resistance]

The evaluation of etching resistance was performed according to the following procedure.

First, an underlayer film of novolac was prepared under the same conditions as those in Example 1 except that novolac (PSM4357 produced by Gunei Chemical Industry Co., Ltd.) was used instead of the compound (BisP-1) of Example 1. Then, the etching test was performed with respect to the underlayer film of novolac, and the etching rate in that time was measured.

Then, the etching test was performed in the same manner with respect to the underlayer films of Example 1 and Comparative Example 1, and the etching rates were measured.

Then, the etching resistances were evaluated according to the following criteria based on the etching rate of the underlayer film of novolac.

<Evaluation Criteria>

A: etching rate of less than −10% compared with the underlayer film of novolac

B: etching rate of −10% to +5% compared with underlayer film of novolac

C: etching rate of more than +5% compared with the underlayer film of novolac

TABLE 1

| | Compound or Resin (parts by mass) | Organic solvent (parts by mass) | Acid generating agent (parts by mass) | Crosslinking agent (parts by mass) | Evaluation of etching resistance |
|---|---|---|---|---|---|
| Example 1 | BisP-1 (10) | CHN (90) | DTDPI (0.5) | Nikalac (0.5) | A |
| Comparative Example 1 | CR-1 (10) | CHN (90) | DTDPI (0.5) | Nikalac (0.5) | C |

Example 2

Then, the solution of the material for forming an underlayer film for lithography in each of Example 1 was coated on a SiO$_2$ substrate having a film thickness of 300 nm, and baked at 240° C. for 60 seconds and further at 400° C. for 120 seconds to thereby form an underlayer film having a film thickness of 80 nm. A resist solution for ArF was coated on the underlayer film, and baked at 130° C. for 60 seconds to thereby form a photoresist layer having a film thickness of 150 nm. Herein, as the resist solution for ArF, one prepared by blending 5 parts by mass of the compound of the following formula (11), 1 part by mass of triphenylsulfonium nonafluoromethanesulfonate, 2 parts by mass of tributylamine, and 92 parts by mass of PGMEA was used.

Herein, the compound represented by the following formula (11) was prepared as follows. That is, 4.15 g of 2-methyl-2-methacryloyloxyadamantane, 3.00 g of methacryloyloxy-γ-butyrolactone, 2.08 g of 3-hydroxy-1-adamantyl methacrylate and 0.38 g of azobisisobutyronitrile were dissolved in 80 mL of tetrahydrofuran to provide a reaction solution. This reaction solution was subjected to polymerization under a nitrogen atmosphere for 22 hours with the reaction temperature being kept at 63° C., and thereafter the reaction solution was dropped in 400 mL of n-hexane. The resin thus obtained was solidified and purified, and a white powder produced was subjected to filtering and dried at 40° C. under reduced pressure overnight to provide the compound represented by the following formula (11).

[Formula 28]

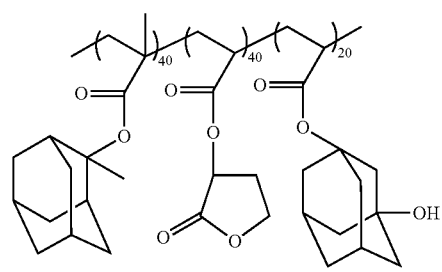

(11)

(in the formula (11), the numerals 40, 40, and 20 indicate the proportions of the respective constituent units, and do not mean a block copolymer.)

Then, the photoresist layer was exposed by using an electron beam lithography apparatus (ELS-7500, produced by Elionix, Inc., 50 keV), baked at 115° C. for 90 seconds (PEB), and developed with a 2.38% by mass aqueous tetramethylammonium hydroxide (TMAH) solution for 60 seconds, thereby providing a positive-type resist pattern.

Comparative Example 2

Except that no underlayer film was formed, the same manner as in Example 2 was performed to form a photoresist layer on a SiO$_2$ substrate to provide a positive-type resist pattern.

[Evaluation]

The shapes of the resist patterns of 55 nm L/S (1:1) and 80 nm L/S (1:1) provided in each of Example 2 and Comparative Example 2 were observed using an electron microscope (S-4800) manufactured by Hitachi Ltd. With respect to the shape of the resist pattern after development, a shape having no pattern collapse and having a good rectangle property was evaluated as being good, and a shape not having such properties was evaluated as being poor. In the observation results, the smallest line width in which no pattern collapse was observed and a good rectangle property was achieved was defined as an evaluation index of resolution. Furthermore, the smallest amount of electron beam energy in which a good pattern shape could be drawn was defined as an evaluation index of sensitivity. The results are shown in Table 2.

TABLE 2

| | Material for forming underlayer film | Resolution (nmL/S) | Sensitivity (μC/cm$^2$) | Resist pattern formation after development |
|---|---|---|---|---|
| Example 2 | Material described in Table 1 (Example 1) | 55 | 12 | Good |
| Comparative Example 2 | Not used | 80 | 26 | Poor |

As can be seen from Table 2, it was confirmed that the underlayer films of Example 2 were significantly excellent in resolution and sensitivity as compared with Comparative Example 2. In addition, it was confirmed that the shape of the resist pattern after development had also no pattern collapse and a good rectangle property. Furthermore, it was shown from the difference from the shape of the resist pattern after development that the material for forming an underlayer film for lithography in each of Example 1 had good adhesiveness with a resist material.

Example 3

The solution of the material for forming an underlayer film for lithography in each of Example 1 was coated on a SiO$_2$ substrate having a film thickness of 300 nm. Then, the solution of the material coated on the substrate was baked at 240° C. for 60 seconds and further at 400° C. for 120 seconds to thereby form an underlayer film having a film thickness of 80 nm. A silicon-containing intermediate layer material was coated on the underlayer film, and baked at 200° C. for 60 seconds to thereby form an intermediate layer film having a film thickness of 35 nm. Furthermore, the resist solution for ArF used in Example 2 was coated on the intermediate layer film, and baked at 130° C. for 60 seconds to thereby form a photoresist layer having a film thickness of 150 nm. Herein, as the silicon-containing intermediate layer material, a silicon atom-containing polymer described in <Synthesis Example 1> in Japanese Patent Laid-Open No. 2007-226170 was used.

Then, the photoresist layer was exposed by using an electron beam lithography apparatus (ELS-7500, produced by Elionix, Inc., 50 keV), baked at 115° C. for 90 seconds (PEB), and developed with a 2.38% by mass aqueous tetramethylammonium hydroxide (TMAH) solution for 60 seconds, thereby providing a positive-type resist pattern of 55 nmL/S (1:1).

Thereafter, the silicon-containing intermediate layer film (SOG) was subjected to dry etching processing while the obtained resist pattern functioned as a mask, using RIE-10NR manufactured by Samco Inc. Subsequently, dry etching processing of the underlayer film while the obtained silicon-containing intermediate layer film pattern functioned as a mask, and dry etching processing of the $SiO_2$ film while the obtained underlayer film pattern functioned as a mask were performed, sequentially.

The respective etching conditions are shown as follows.
Conditions of resist pattern etching on resist intermediate layer film
  Output: 50 W
  Pressure: 20 Pa
  Time: 1 min
  Etching Gas
  Ar gas flow rate:$CF_4$ gas flow rate:$O_2$ gas flow rate=50:8:2 (sccm)
Conditions of resist intermediate film pattern etching on resist underlayer film
  Output: 50 W
  Pressure: 20 Pa
  Time: 2 min
  Etching Gas
  Ar gas flow rate:$CF_4$ gas flow rate:$O_2$ gas flow rate=50:5:5 (sccm)
Conditions of resist underlayer film pattern etching on $SiO_2$ film
  Output: 50 W
  Pressure: 20 Pa
  Time: 2 min
  Etching Gas
  Ar gas flow rate:$C_5F_{12}$ gas flow rate:$C_2F_6$ gas flow rate:$O_2$ gas flow rate=50:4:3:1 (sccm)
[Evaluation]

The cross section of the pattern (the shape of the $SiO_2$ film after etching) of each of Example 3 obtained as described above was observed using an electron microscope (S-4800) manufactured by Hitachi Ltd. As a result, it was confirmed that the shape of the $SiO_2$ film after etching in multilayer resist processing was rectangular with no defects observed, and the cross section shape of the pattern was also good in Example 3 using the underlayer film of the present invention.

As described above, the present invention is not limited to the embodiments and Examples, and can be appropriately modified without departing the gist thereof.

The present application is based on Japanese Patent Application (Japanese Patent Application No. 2013-023529) filed on Feb. 8, 2013, and the content thereof is herein incorporated by reference.

The material for forming an underlayer film for lithography and the underlayer film of the present invention have a relatively high carbon concentration, a relatively low oxygen concentration, a relatively high heat resistance and also a relatively high solvent solubility, and which can be applied to a wet process. Therefore, the material for forming an underlayer film for lithography and the underlayer film of the present invention can be widely and effectively utilized in various applications in which these properties are required. Therefore, the present invention can be widely and effectively utilized for, for example, an electric insulating material; a resist resin; a sealing resin for a semiconductor; an adhesive for a printed wiring board; an electric laminated board mounted on electrical equipment, electronic equipment, industrial equipment and the like; a matrix resin for a prepreg mounted on electrical equipment, electronic equipment, industrial equipment and the like; a material for a build-up laminated board; a resin for fiber-reinforced plastics; a sealing resin for a liquid crystal display panel; a paint; various coating agents; an adhesive; a coating agent for a semiconductor; a resist resin for a semiconductor; and a resin for forming an underlayer film. In particular, the present invention can be particularly effectively utilized in the field of an underlayer film for lithography and an underlayer film for a multilayer resist.

The invention claimed is:

1. A material for forming an underlayer film for lithography comprising:
an acid generating agent and a crosslinking agent; and
a compound represented by the following general formula (1):

[Formula 1]

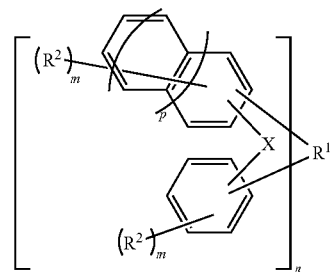

in formula (1), each X independently represents an oxygen atom or a sulfur atom, $R^1$ represents a single bond or a 2n-valent hydrocarbon group having 1 to 30 carbon atoms, the hydrocarbon group may have a cyclic hydrocarbon group, a double bond, a hetero atom or an aromatic group having 6 to 30 carbon atoms, and each $R^2$ independently represents a linear, branched or cyclic alkyl group having 1 to 10 carbon atoms, an aryl group having 6 to 10 carbon atoms, an alkenyl group having 2 to 10 carbon atoms, or a hydroxyl group, provided that at least one $R^2$ represents a hydroxyl group, each m is independently an integer of 1 to 4, n is an integer of 1 to 4, and p is 0 or 1.

2. The material for forming the underlayer film for lithography according to claim 1, wherein the compound represented by the general formula (1) comprises at least one of compounds represented by the following general formula (1a) and general formula (1b):

[Formula 2]

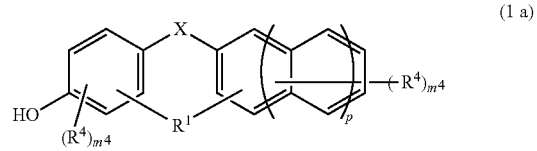

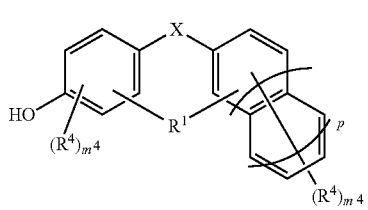

in formula (1a) and formula (1b), X represents an oxygen atom or a sulfur atom, $R^1$ represents a single bond or a 2-valent hydrocarbon group having 1 to 30 carbon atoms, the hydrocarbon group may have a cyclic hydrocarbon group, a double bond, a hetero atom or an aromatic group having 6 to 30 carbon atoms, each $R^4$ independently represents a linear, branched or cyclic alkyl group having 1 to 10 carbon atoms, an aryl group having 6 to 10 carbon atoms, an alkenyl group having 2 to 10 carbon atoms, or a hydroxyl group, each $m^4$ is independently an integer of 0 to 3, and p is 0 or 1.

3. The material for forming the underlayer film for lithography according to claim 1, further comprising an organic solvent.

4. The material for forming the underlayer film for lithography according to claim 1, wherein the amount of the acid generating agent is 0.1-50 parts by mass based on 100 parts by mass of the compound represented by the general formula (1).

5. The material for forming the underlayer film for lithography according to claim 4, wherein the amount of the acid generating agent is 30-50 parts by mass based on 100 parts by mass of the compound represented by the general formula (1).

6. An underlayer film for lithography, formed from the material for forming the underlayer film for lithography according to claim 1.

7. A pattern forming method, comprising:
step (A-1) of forming an underlayer film on a substrate by using the material for forming the underlayer film according to claim 1;
step (A-2) of forming at least one photoresist layer on the underlayer film; and
step (A-3) of irradiating a predetermined region of the photoresist layer with radiation followed by developing with an alkali, after step (A-2),
wherein the material for forming the underlayer film is crosslinked.

8. A pattern forming method, comprising
step (B-1) of forming an underlayer film on a substrate by using the material for forming the underlayer film according to claim 1;
step (B-2) of forming an intermediate layer film on the underlayer film by using a silicon atom-containing resist intermediate layer film material;
step (B-3) of forming at least one photoresist layer on the intermediate layer film;
step (B-4) of irradiating a predetermined region of the photoresist layer with radiation followed by developing with an alkali to form a resist pattern, after step (B-3); and
step (B-5) of etching the intermediate layer film while the resist pattern functions as a mask, etching the underlayer film while the obtained intermediate layer film pattern functions as an etching mask and etching the substrate while the obtained underlayer film pattern functions as an etching mask to form a pattern on the substrate, after step (B-4),
wherein the material for forming the underlayer film is crosslinked.

9. A material for forming an underlayer film for lithography, comprising:
an acid generating agent and a crosslinking agent; and
a resin having a structure represented by the following general formula (2)

[Formula 3]

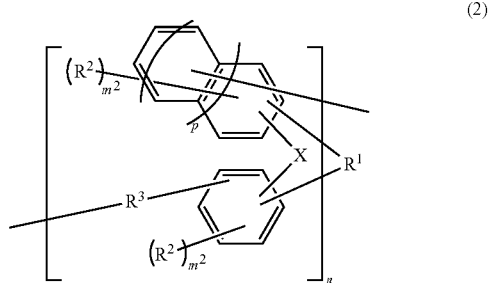

in formula (2), each X independently represents an oxygen atom or a sulfur atom, $R^1$ represents a single bond or a 2n-valent hydrocarbon group having 1 to 30 carbon atoms, the hydrocarbon group may have a cyclic hydrocarbon group, a double bond, a hetero atom or an aromatic group having 6 to 30 carbon atoms, and each $R^2$ independently represents a linear, branched or cyclic alkyl group having 1 to 10 carbon atoms, an aryl group having 6 to 10 carbon atoms, an alkenyl group having 2 to 10 carbon atoms, or a hydroxyl group, provided that at least one $R^2$ represents a hydroxyl group, each $R^3$ independently represents a single bond, or a linear or branched alkylene group having 1 to 20 carbon atoms, each $m^2$ is independently an integer of 1 to 3, n is an integer of 1 to 4, and p is 0 or 1.

10. A method for forming an underlayer film for lithography, the method comprising:
applying to a substrate a composition comprising an acid generating agent, a crosslinking agent, and a compound represented by the following formula (1):

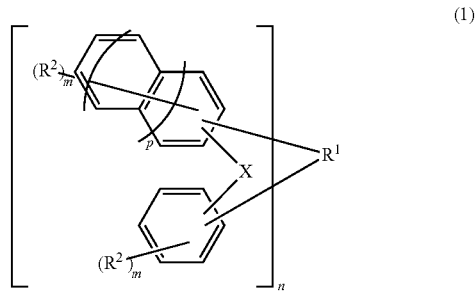

wherein each X independently represents an oxygen atom or a sulfur atom, $R^1$ represents a single bond or a 2n-valent hydrocarbon group having 1 to 30 carbon atoms, the hydrocarbon group may have a cyclic hydrocarbon group, a double bond, a hetero atom or an aromatic group having 6 to 30 carbon atoms, and each $R^2$ independently represents a linear, branched or cyclic alkyl group having 1 to 10 carbon atoms, an aryl group having 6 to 10 carbon atoms, an alkenyl group having 2 to 10 carbon atoms, or a hydroxyl group, provided that at least one $R^2$ represents a hydroxyl group, each m is independently an integer of 1 to 4, n is an integer of 1 to 4, and p is 0 or 1; and crosslinking the composition.

* * * * *